(12) United States Patent
Shemi

(10) Patent No.: US 8,999,945 B2
(45) Date of Patent: *Apr. 7, 2015

(54) METHODS, COMPOSITIONS AND SYSTEMS FOR LOCAL DELIVERY OF DRUGS

(75) Inventor: Amotz Shemi, Herzliya (IL)

(73) Assignee: Silenseed Ltd, Jerusalem (IL)

( * ) Notice: Subject to any disclaimer, the term of this patent is extended or adjusted under 35 U.S.C. 154(b) by 270 days.

This patent is subject to a terminal disclaimer.

(21) Appl. No.: 13/000,656

(22) PCT Filed: Jun. 28, 2009

(86) PCT No.: PCT/IB2009/052778
§ 371 (c)(1),
(2), (4) Date: Dec. 22, 2010

(87) PCT Pub. No.: WO2010/001325
PCT Pub. Date: Jan. 7, 2010

(65) Prior Publication Data
US 2011/0195123 A1    Aug. 11, 2011

Related U.S. Application Data

(60) Provisional application No. 61/129,477, filed on Jun. 30, 2008.

(51) Int. Cl.
| | | |
|---|---|---|
| *A61K 31/713* | (2006.01) | |
| *A61K 9/00* | (2006.01) | |
| *A61K 48/00* | (2006.01) | |
| *A61K 31/74* | (2006.01) | |
| *C12N 15/113* | (2010.01) | |
| *A61K 47/34* | (2006.01) | |

(52) U.S. Cl.
CPC .............. *A61K 9/0024* (2013.01); *A61K 47/34* (2013.01)

(58) Field of Classification Search
None
See application file for complete search history.

(56) References Cited

U.S. PATENT DOCUMENTS

| | | | | |
|---|---|---|---|---|
| 5,801,154 | A * | 9/1998 | Baracchini et al. | 514/44 A |
| 6,514,193 | B2 * | 2/2003 | Kaplan | 600/7 |
| 2004/0063654 | A1 * | 4/2004 | Davis et al. | 514/44 |
| 2004/0121348 | A1 * | 6/2004 | Kreutzer et al. | 435/6 |
| 2006/0115455 | A1 * | 6/2006 | Reed et al. | 424/93.2 |
| 2006/0228404 | A1 * | 10/2006 | Anderson et al. | 424/450 |
| 2007/0207211 | A1 * | 9/2007 | Zeigerson | 424/489 |
| 2008/0008733 | A1 * | 1/2008 | Bechet et al. | 424/422 |
| 2008/0097280 | A1 * | 4/2008 | Martin et al. | 604/21 |
| 2008/0124370 | A1 | 5/2008 | Marx | |
| 2009/0149569 | A1 * | 6/2009 | Shastri et al. | 523/113 |
| 2009/0286847 | A1 * | 11/2009 | Fang et al. | 514/415 |
| 2010/0204297 | A1 * | 8/2010 | Chen et al. | 514/44 A |

FOREIGN PATENT DOCUMENTS

| | | |
|---|---|---|
| CA | 2621055 | 3/2007 |
| JP | 9124490 | 5/1997 |
| JP | H09-124490 | 5/1997 |
| WO | WO/02058752 | 8/2002 |
| WO | WO/2008057867 | 5/2008 |
| WO | WO/2008124634 | 10/2008 |

OTHER PUBLICATIONS

Schiffelers et al, Cancer siRNA therapy by tumor selective delivery with ligand-targeted sterically stabilized nanoparticle, Nucleic Acids Research, 2004, vol. 32, No. 19 e149, pp. 1-10.*
Weinberg et al, Development and Characterization of Dual-Release Poly(D,L-lactide-co-glycolide) Millirods for Tumor Treatment, In Polymeric Drug Delivery II; Svenson, S.;pp. 169-185, ACS Symposium Series; American Chemical Society: Washington, DC, 2006.*
Sawyer et al, New Methods for Direct Delivery of Chemotherapy for Treating Brain Tumors, Yale Journal of Biology and Medicine 79 (2006), pp. 141-152.*
Khan et al, Sustained Polymeric Delivery of Gene Silencing Antisense ODNs, siRNA, DNAzymes and Ribozymes: In Vitro and In Vivo StudiesJournal of Drug Targeting, Jul. 2004 vol. 12 (6), pp. 393-404.*
Wang et al, Modulating b-Lapachone Release from Polymer Millirods through Cyclodextrin Complexation, Journal of Pharmaceutical Sciences, vol. 95, No. 10, Oct. 2006, pp. 2309-2319.*
Xie et al, Electrospun Micro- and Nanofibers for Sustained Delivery of Paclitaxel to Treat C6 Glioma in Vitro, Pharmaceutical Research, vol. 23, No. 8, Aug. 2006, pp. 1817-1826.*
Bennett and Cowsert (Biochimica et Biophysica Acta, 1999, pp. 19-30; see entered document).*
Murata et al: "Anti-tumor effects of anti-VEGF siRNA encapsulated with PLGA microspheres in mice" Journal of Controlled Release, Elsevier, Amsterdam, NL LNKD—DOI:10.1016/J.JCORNEL.2007. 11.017, vol. 126, No. 3, Dec. 8, 2007, pp. 246-254, XP022502654 ISSN: 0168-3659 p. 247-p. 250.
Khan A et al: "Sustained polymeric delivery of gene silencing antisense ODNs, siRNA, DNAzymes and Ribozymes: in vitro and in vivo studies" Journal of Drug Targeting, Harwood Academic Publishers GMBH, DE, vol. 12, No. 6, Jul. 1, 2004, pp. 393-404, XP003002819 ISSN: 1061-186X p. 398.
Database WPI Week 199729 Thomson Scientific, London GB; AN 1997-316481 XP002603308.
Gary et al. "Polymer-based siRNA delivery: Perspectives on the fundamental and phenomenological distinctions from polymer-based DNA delivery" J. Controlled Release 121:64-73 (2007).
Imamura et al. "siRNA-mediated *Erc* gene silencing suppresses tumor growth in Tsc2 mutant renal carcinoma model" Cancer Lett. 268:278-285 (2008).

* cited by examiner

*Primary Examiner* — Maria Marvich

(74) *Attorney, Agent, or Firm* — JMB Davis Ben-David

(57) ABSTRACT

Implantable medical device eluting drug locally and in a prolonged fashion are provided.

14 Claims, 32 Drawing Sheets

METHODS, COMPOSITIONS AND SYSTEMS FOR LOCAL DELIVERY OF DRUGS

CROSS REFERENCE TO RELATED APPLICATIONS

This application is a national stage application claiming priority to international patent application No. PCT/IB2009/052778 filed on Jun. 28, 2009 which in turn claimed priority to U.S. patent Application No. 61/129,477 filed on Jun. 30, 2008.

SUBMISSION OF SEQUENCE LISTING

The present application is being filed along with a Sequence Listing in electronic format via EFS-Web. The Sequence Listing is provided as a text file entitled SequenceListing.txt. That text file is 4 Kb in size and was created Mar. 7, 2011. The information in the electronic format of the Sequence Listing is incorporated herein by reference in its entirety into this specification.

FIELD OF THE INVENTION

The present invention is of a method, system and composition for local/regional delivery of nucleotide based therapeutic agents, and in particular, for such a method, system and composition for RNA interference (RNAi) therapeutic agents.

BACKGROUND OF THE INVENTION

The recent advance in research and clinical trials of plurality of small interference RNA (siRNA) drugs raised the odds to transfer siRNA to true therapeutic treatment (1-4). RNAi is proved as a robust mode of action for gene silencing. The effect was proven experimentally in suppressing tumor growth, by targeting oncogenes or tumor growth factors. RNAi through synthetic siRNA or from expression vectors for short hairpin RNA (shRNA) is able to silence targets such as VEGF; an important actors for angiogenesis both for regenerative purposes and at pathological cases such as a tumor and diabetic retinopathy. The effect was also shown in humans. The delivery methods in development of siRNA drugs are varied, including systemic administration of naked or modified siRNA, or DNA expressing shRNA (mainly for in-vivo tests); non-viral methods including nano-particles, systemic administration of liposomes encapsulating si/shRNA; applying viral vectors as delivery methods; or various physical or chemical supported delivery systems like laser beam gene transfer (LBGT) (5). Still, all such delivery methods share the same main disadvantage (6). All administration methods, whether systemic or through direct injection, suffer from poor targeting, immune stimulation, enzymatic degradation, toxic reactions, inability to penetrate tissue and/or cellular barriers to delivery, inefficiency of gene silencing due to non constant rate of release, may be very expensive, or suffer from inefficiency/major side effects upon local administration such as in the case of electroporation or ultrasound mediated vascular transduction.

SUMMARY OF THE INVENTION

The background art does not teach or suggest a method, system and composition for local delivery of nucleotide based therapeutic agents, which overcomes the disadvantages of systemic delivery and of direct injection.

Provided is an implantable medical device eluting drug locally and in prolonged period, including several types of such a device, treatment modes of implementation, and methods of implantation. The device is comprised of polymeric substrate, such as a matrix for example, that is used as the device body; drugs; in some cases additional scaffolding materials, such as metals or additional polymers; and materials to enhance visibility and imaging. Selection of the drug is based on the advantages of releasing drug locally and in prolonged period, where drug is released directly to the extracellular matrix (ECM) of the diseased area such as for tumor, inflammation, or degeneration, for symptomatic objectives, to injured smooth muscle cells, or for prevention. One kind of drug is the gene silencing drugs based on RNA interference (RNAi), including but not limited to siRNA, shRNA, or antisense RNA/DNA, ribozyme, and nucleoside analogs. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

The present invention provides a method, system and composition for local (and optionally regional) and prolonged delivery of nucleotide based therapeutic agents such as siRNA or shRNA for example. By "nucleotide based therapeutic agent" it is meant any such agent which includes at least one nucleotide, whether natural or non-natural. Non-limiting examples of such agents include but are not limited to any type of RNA interfering (RNAi) agents, whether single stranded or double stranded, that perform gene cessation and/or gene knockdown, including gene knockdown of message (mRNA) by degradation or translational arrest of the mRNA, inhibition of tRNA and rRNA functions or epigenetic effects; short (or small) interfering RNA (siRNA), short hairpin RNA (shRNA), microRNA and non-coding RNA or the like, Short RNAs activity on DNA, and Dicer-substrate siRNAs (DsiRNAs) (DsiRNA are cleaved by the RNase III class endoribonuclease dicer into 21-23 base duplexes having 2-base 3'-overhangs siRNA), and UsiRNA (UsiRNAs are duplex siRNAs that are modified with non-nucleotide acyclic monomers, termed unlocked nucleobase analogs (UNA), in which the bond between two adjacent carbon atoms of ribose is removed); and Self-delivering RNA (sdRNA) including rxRNA™ (of RXi Therapeutics), and agents inhibiting the pre-mRNA maturation step of polyA tail addition such as the U1 adaptor (IDT Inc.). The U1 adaptor consists of two parts, a target-gene binding domain and a U'1 domain that attracts and inhibits the cellular splicing apparatus. By combining both capabilities in the same molecule, the U1 adaptor can inhibit the pre-mRNA maturation step of polyA tail addition. Further, the domains of the oligonucleotide are independent so transcript binding and splicing inhibition can be independently optimized and adapted to a wide array of genes.

The agent is preferably delivered, in some embodiments, with a "Loder" (Local Drug EluteR).

In some embodiments, the agent is used to treat cancer. Preferably, the agent is selected specifically for a particular type of cancer and is administered locally at the tumor area, in rate that is preferably maintained above the lower threshold of therapeutic effectiveness for prolonged period, and is constant to a certain level to optimize the effective silencing period.

In other embodiments, the agent is used to relieve chronic pain, prevent the accumulation of toxic metabolites, suppress degenerative processes or attenuate inflammation, attenuate apoptosis and necrosis and prevent and/or decrease infection, inhibit autophagia, dedifferentiation or differentiation of cells.

Optionally, one or more other types of agents may also be included, apart from but in addition to nucleotide based agents, including but not limited to proteins, including but not limited to growth factors, antibodies, cytokines or their derivatives; peptides, whether linear or circular; peptidomimetics, lectins, carbohydrates and lipids.

The additional agent is optionally and preferably selected from the group consisting of anti cancer, chemotherapy, analgesics, anti degenerative, pro-regenerative, antiplatelet drugs, anticoagulant drugs, anti-inflammatory drugs, antireplicate drugs, pro-oxidative, local immune suppression, to generate an immune privileged site, anti-metabolic, anti-infectious including anti viral, anti bacterial, anti fungal and anti parasite, anti-angiogenic, contraceptive, cognitive and combinations of said drugs.

The nucleotide based agent, as noted above, preferably comprises some type of nucleotide and/or oligonucleotide and/or polynucleotide and more preferably also is adjusted to reduce degradation by RNAse, for example through the inclusion of modified nucleotides (including but not limited to 2'OMe and fluorine-CTP and UTP, as examples of 2'F-RNA and partial 2'F-RNA modifications). The drug could optionally be designed with a locked nucleic acid (LNA) and/or peptide nucleic acid (PNA) backbone. The drug could optionally be conjugated to lipid moieties such as cholesterol to improve penetration. The drug could optionally be mixed with cell membrane and endosomal disrupting molecules. The drug could optionally be mixed and/or complexed with natural polymers including spermin and cephalin (phosphatidylethanolamine), or other polymers such as polyethyleneimines (PEI) to improve stability and/or enhance cellular penetration.

The Loder may optionally be used for local administration in that the Loder is inserted locally. The therapeutic agent may optionally be restricted in its effect to the local site of local administration, substantially without significant diffusion from the local site, or alternatively may have systemic effects, optionally including systemic distribution. By "substantially without significant diffusion from the local site", it is meant that the therapeutic agent(s) diffuse only within a limited volume or area around the local site, such that administration is not systemic or at least such that a therapeutically effective concentration is reached only within a limited area surrounding the local site. This limited volume or area is optionally within the distance of 5 cm from the Loder as a non-limiting example of a distance within which the concentration of the agent(s) is optionally and preferably maintained at or above the therapeutic threshold. Typically the concentration of the agent(s) will fall off as a function of distance from the Loder, typically in a non-linear manner.

As described herein, "treatment" also includes prevention.

As used herein, "about" means plus or minus approximately ten percent of the indicated value.

Other features and advantages of the various embodiments of the invention will be apparent from the following detailed description, and from the claims.

BASIC DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

Figure 4:
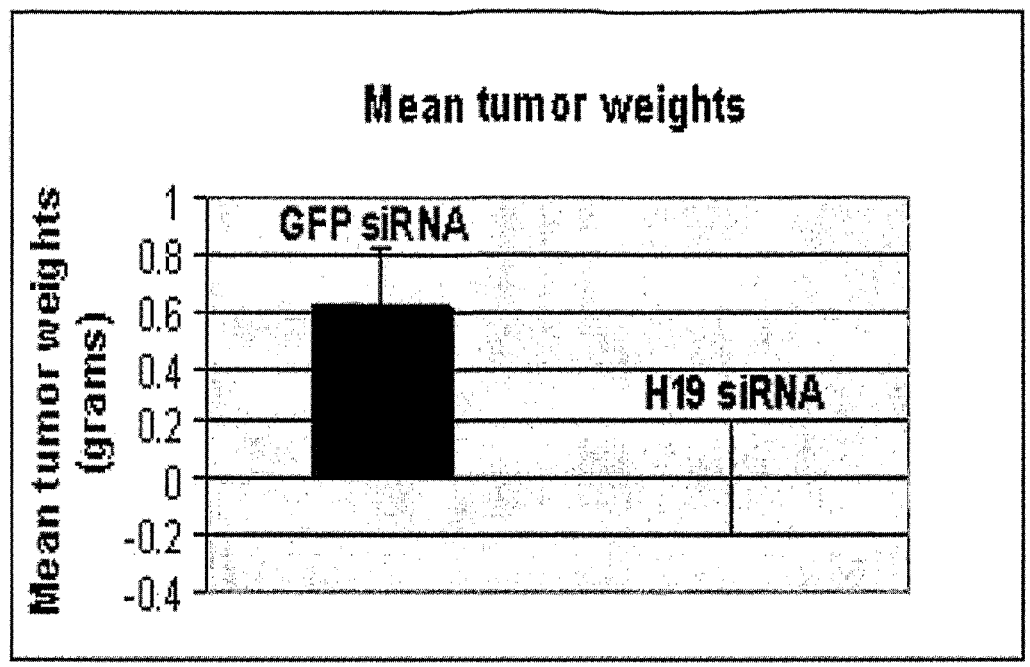
Figure 4:
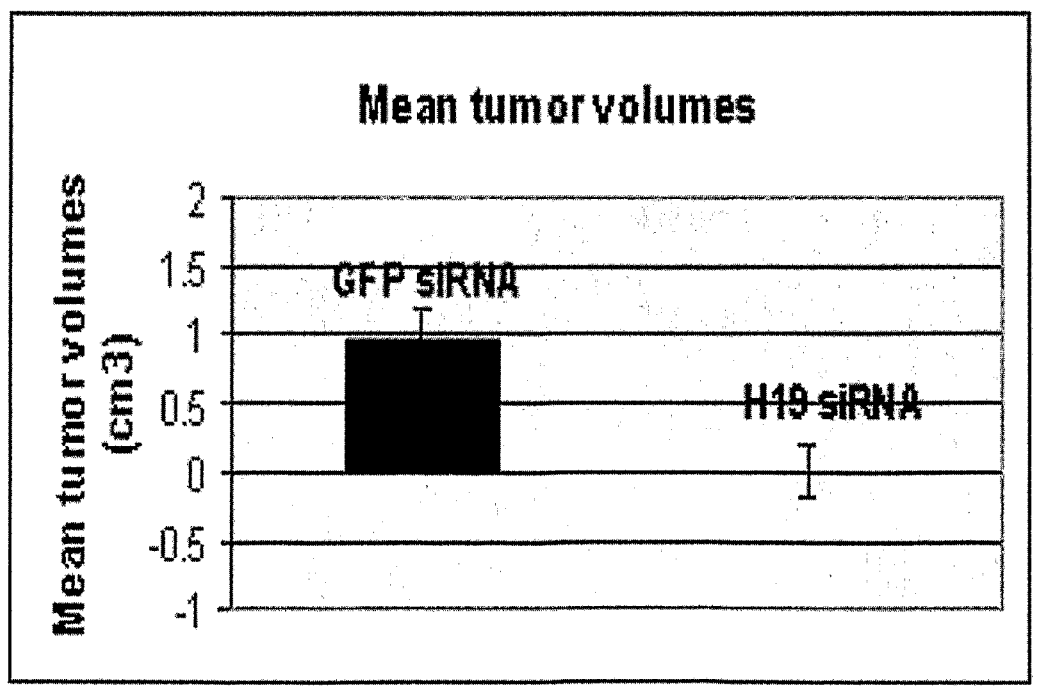
Figure 5:
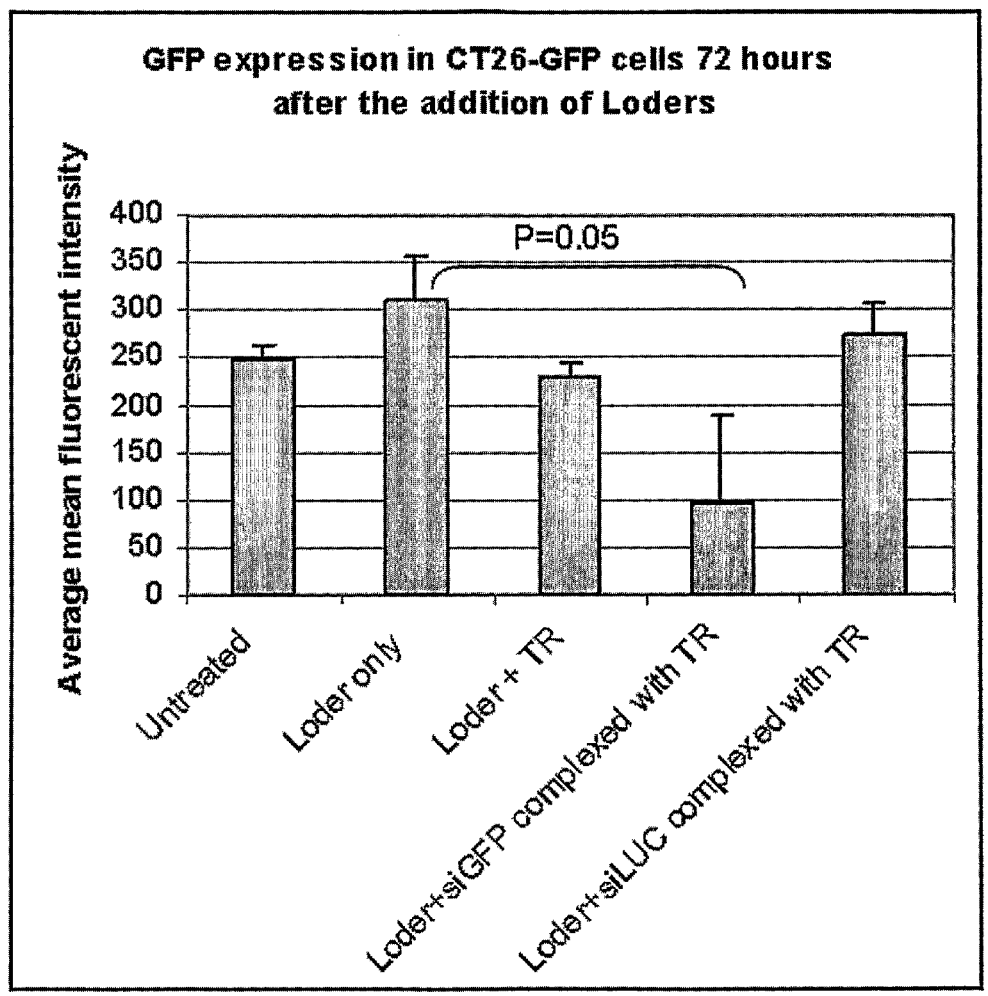
Figure 6:
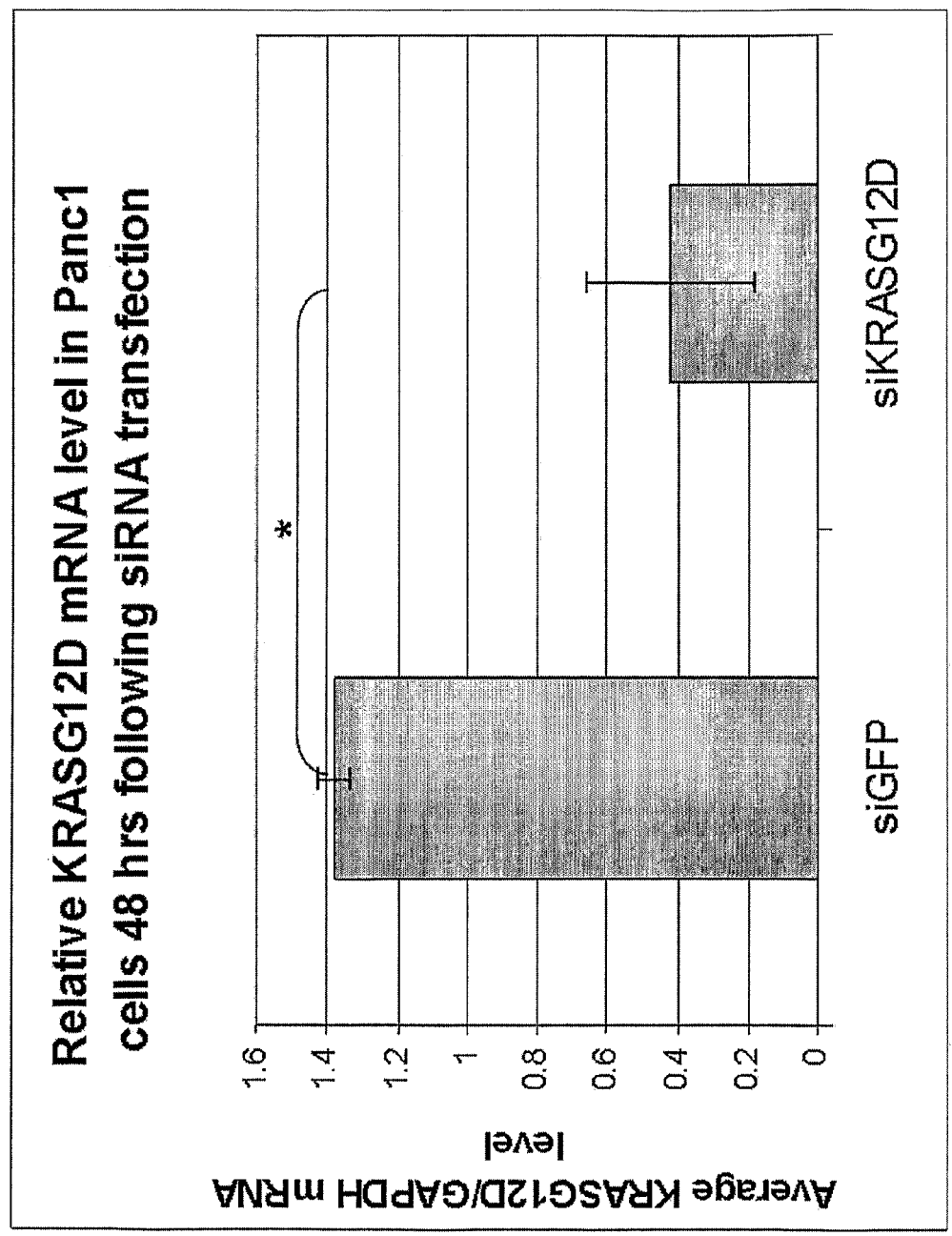
Figure 7:
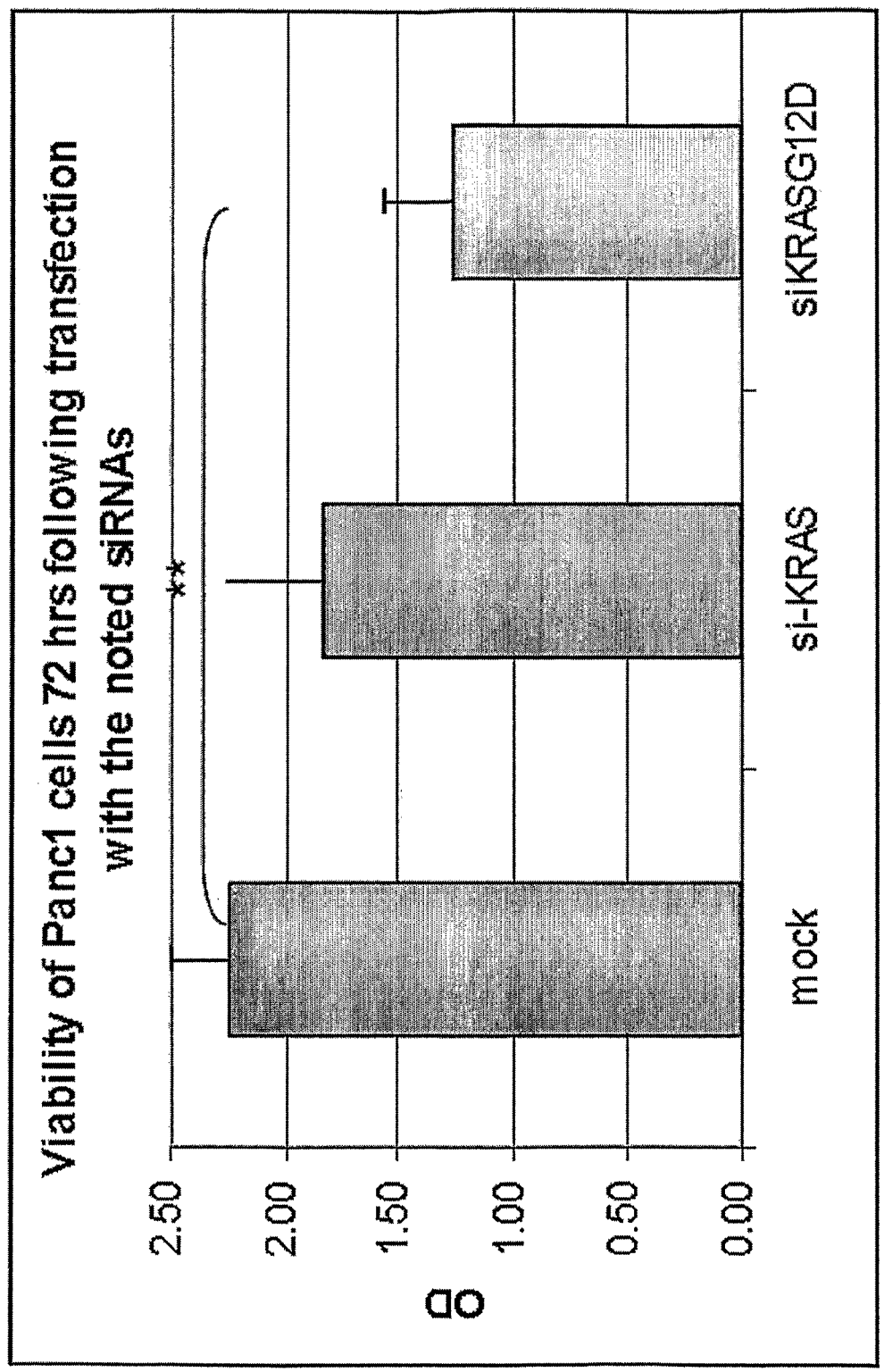
Figure 8:
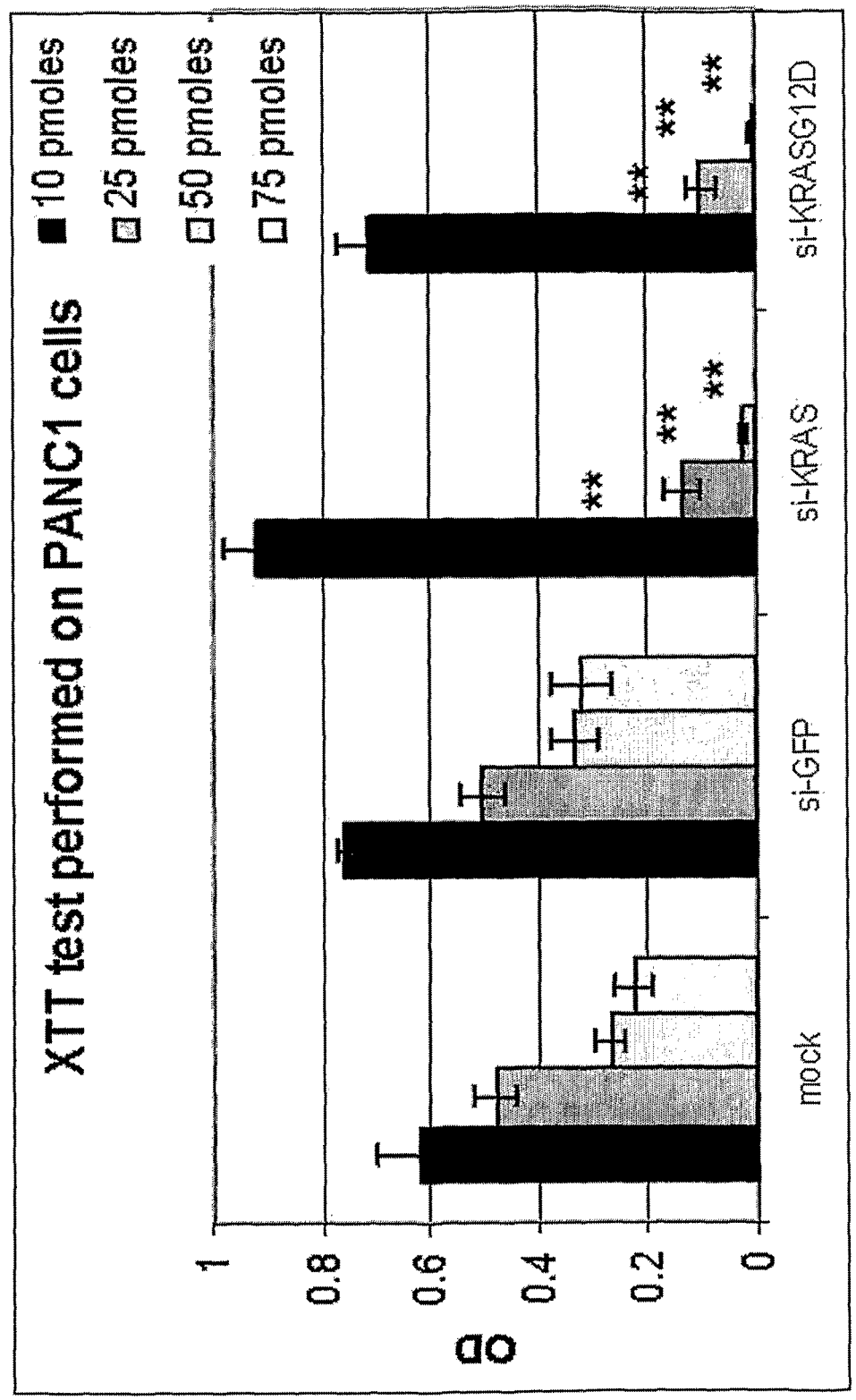
Figure 9:
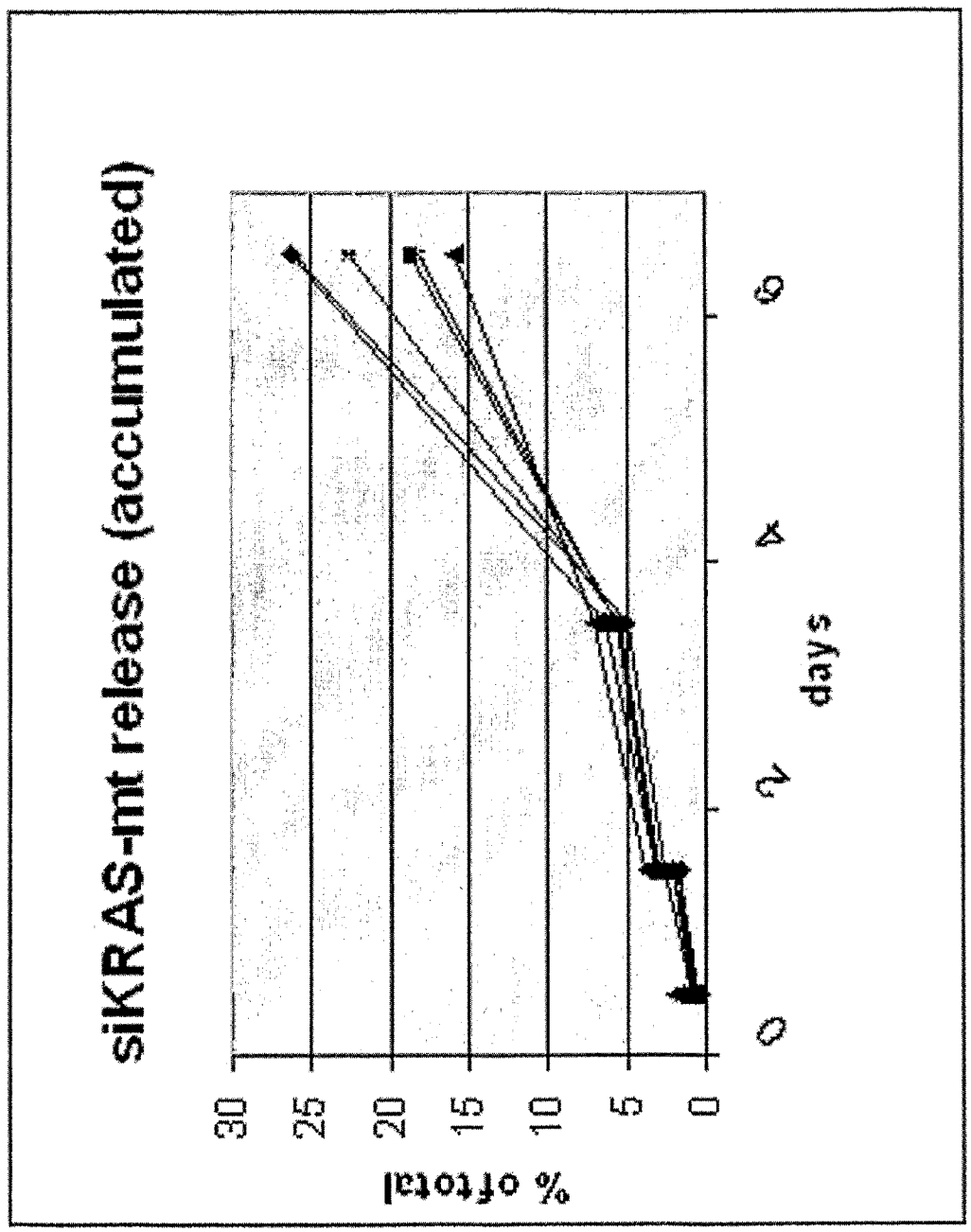
Figure 11A:
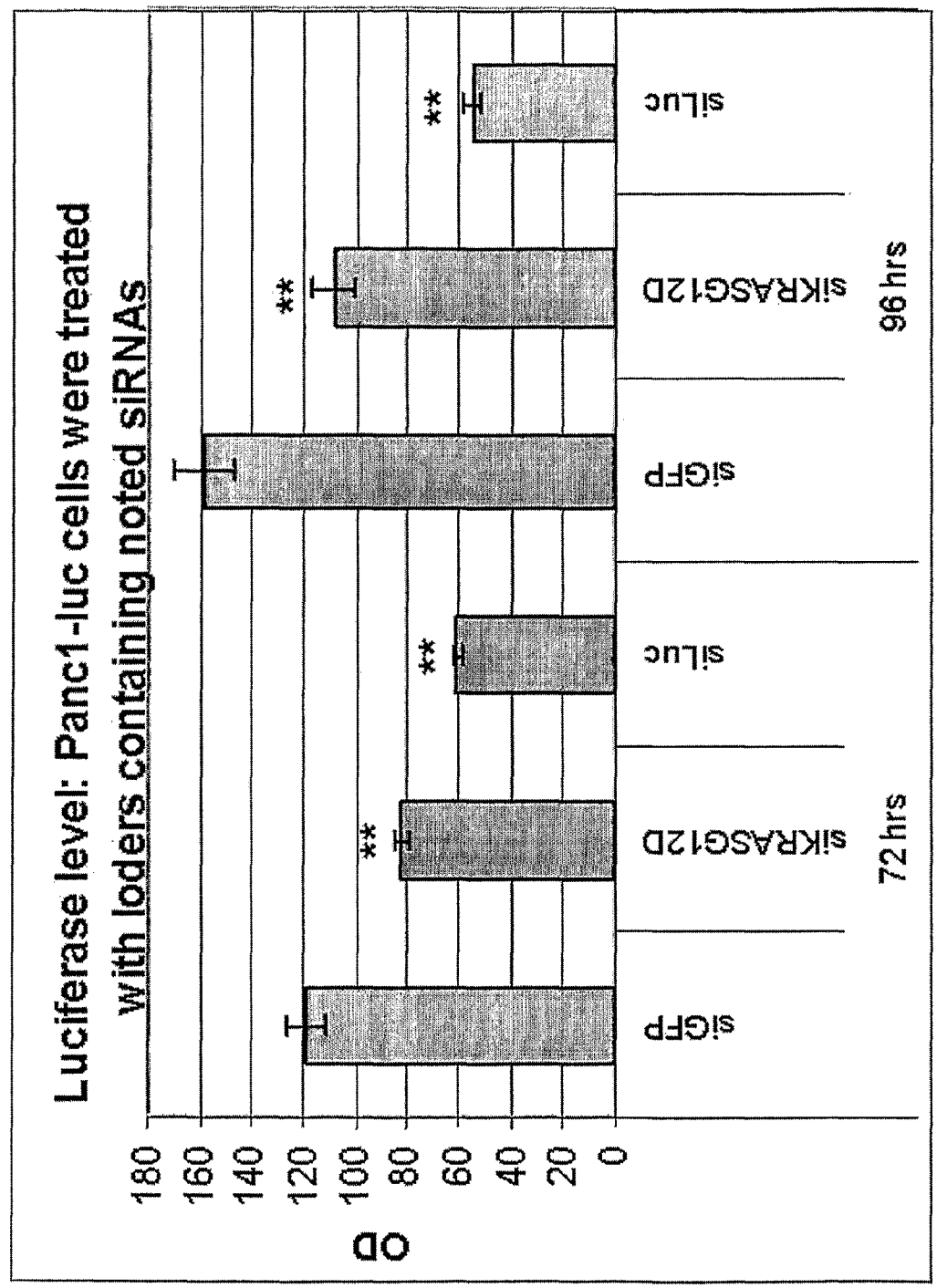
Figure 11B:
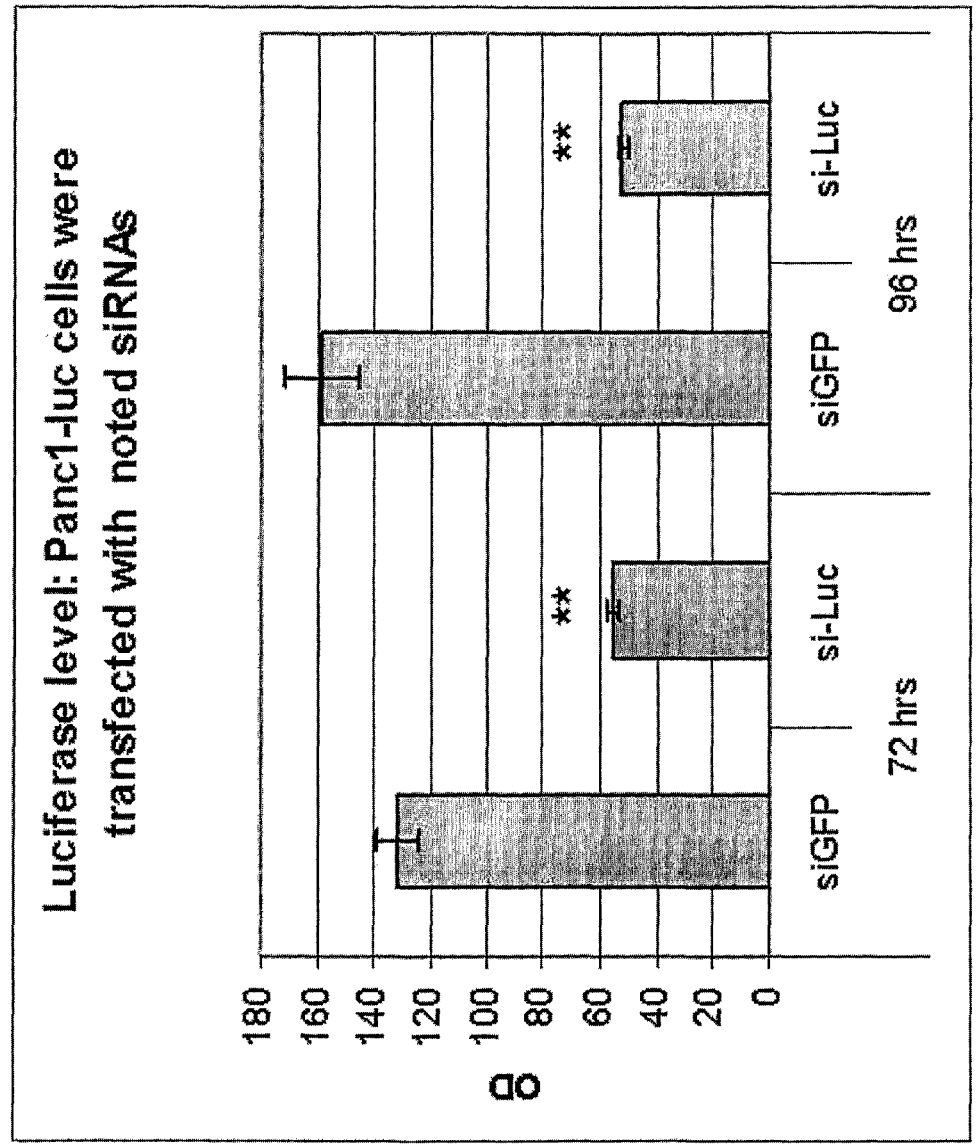

FIG. 4 demonstrates that siRNA-based silencing of H19 impedes tumor growth in vivo;

FIG. 5 demonstrates that siGFP-containing LODER can specifically and potently inhibit GFP expression in vitro;

FIG. 6 shows that siRNA against mutant kRAS(G12D) specifically and potently inhibits the expression of mutant kRAS in vitro. Pancreatic carcinoma Panc1 cells (expressing mutant kRAS(G12D)) were transfected with the indicated siRNAs for 48 hours. Semi-quantitative RT-PCR results of mutant kRAS(G12D) mRNA expression are shown, after normalization to GAPDH;

FIG. 7 shows that inhibition of mutant kRAS impedes pancreatic carcinoma cells (Panc1) growth. Panc1 cells (expressing mutant kRAS(G12D)) were transfected. 72 hours later, XTT test was performed;

FIG. 8 shows that inhibition of mutant kRAS with siRNA impedes Panc1 cells growth in a dose response manner. Panc1 cells (expressing mutant kRAS(G12D)) were transfected with the indicated siRNA doses. XTT test was performed 72 hours later;

FIG. 9 shows curves of cumulative siRNA release for the Loders used in the above experiments;

FIG. 10 shows that Loder-embedded siKRASG12D inhibits Panc1 cell viability and leads to cell death;

FIGS. 11A and 11B show the effect of releasing siRNAs from the Loders on a pancreatic cell line in comparison to transfection with the siRNAs;

FIGS. 12A-12D show Western blots of the results from an experiment performed as previously described for FIG. 10;

FIGS. 13-17 show the effects of siGFP against luciferase luminescence, while

Figure 23:
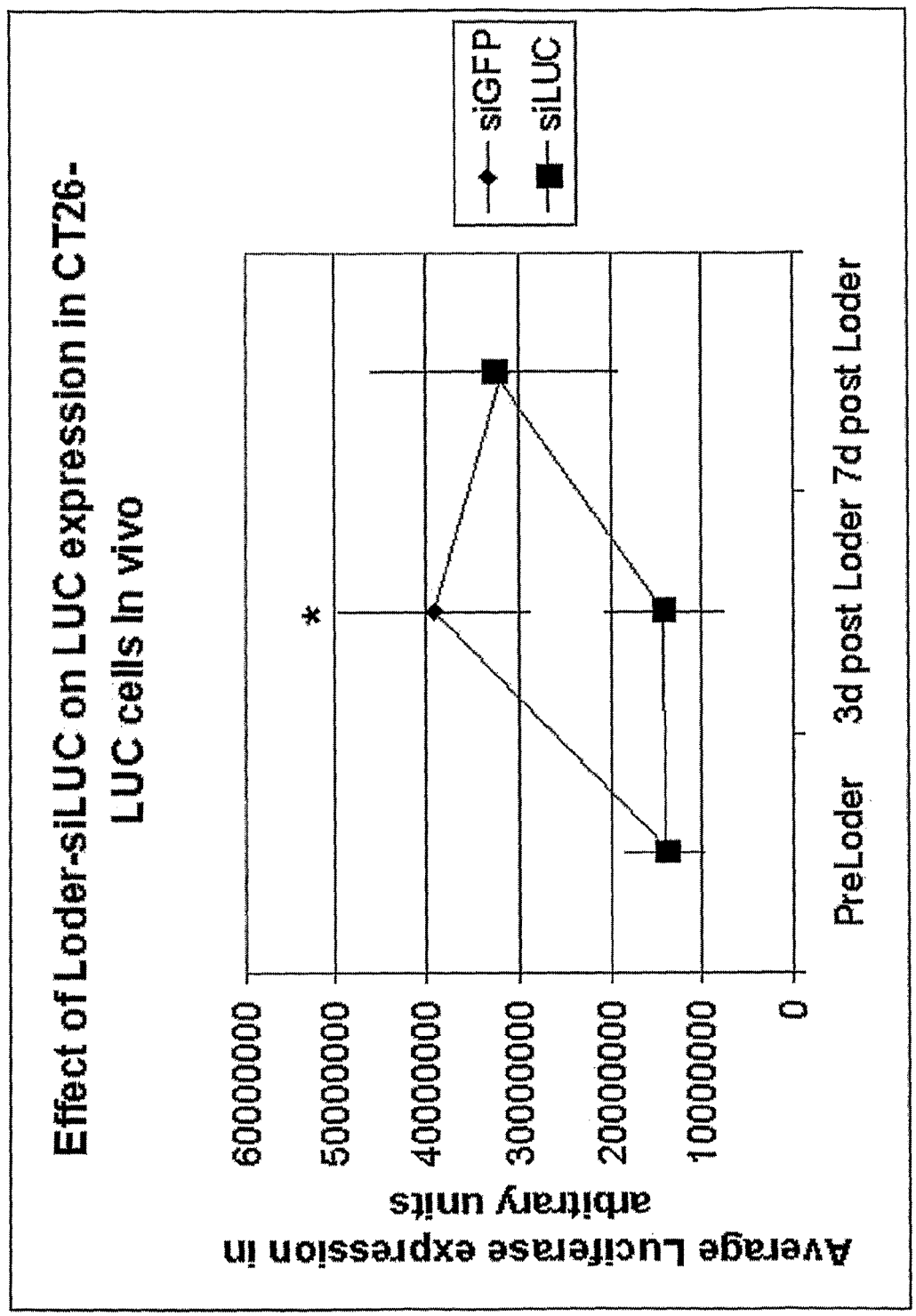
Figure 24:
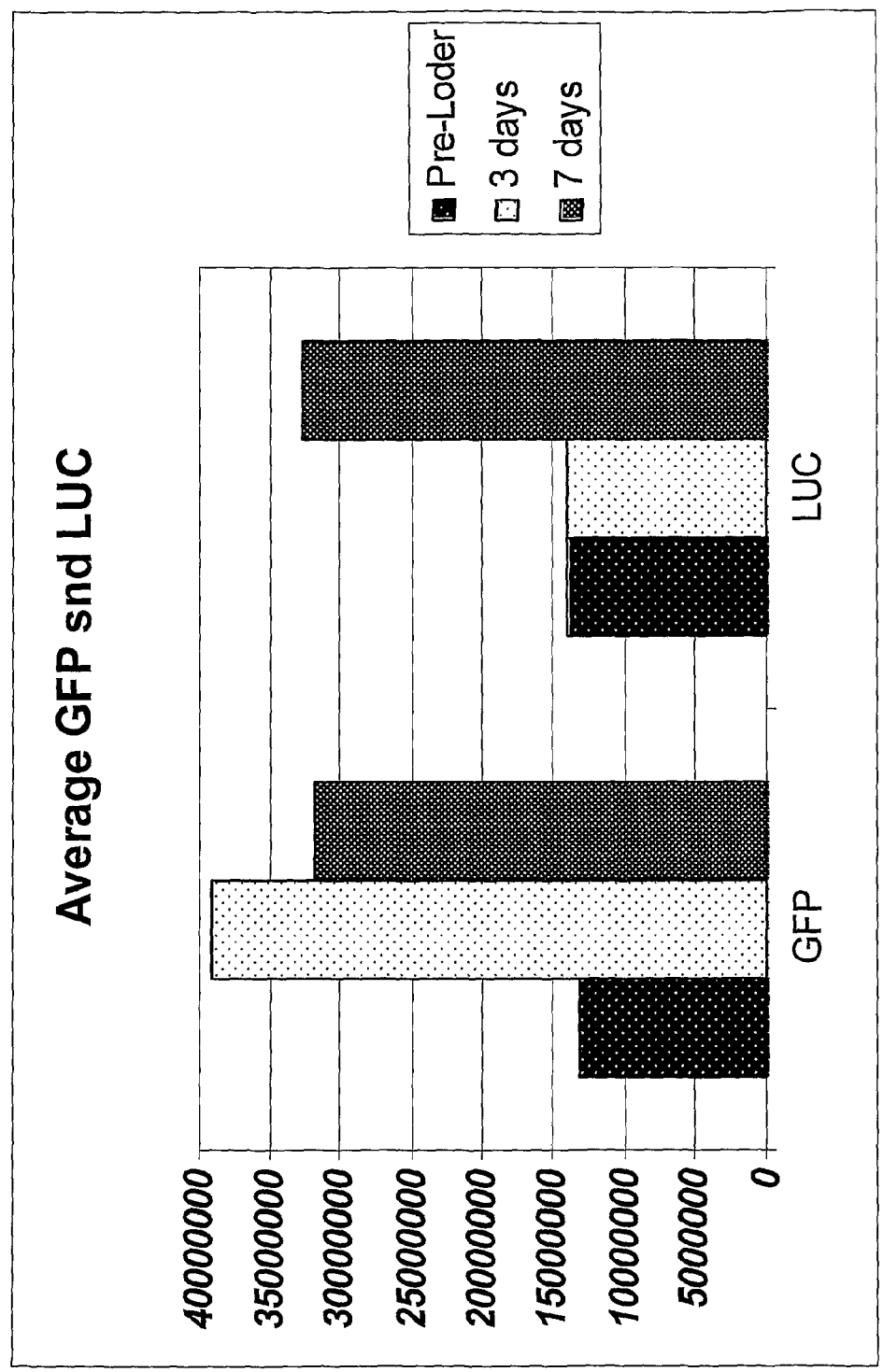

FIGS. 18-22 show the effects of siLUC against luciferase luminescence;

FIG. 23 shows the average intensity of all mice in each group, GFP (mice 1-5) or LUC (mice 6-10), for each day. siLUC has the most significant effect against luminosity around day 3, by preventing a significant increase in luminosity (even though tumor growth itself was not affected); and FIG. 24 shows a graph of the actual luminosity data (y-axis) as opposed to the number of days after initiation of treatment (x-axis), for mice in each group. There is some variability between mice but the overall trend is clear; siLUC had a significant effect in inhibiting luminosity as opposed to siGFP, when delivered in vivo to the site of a tumor by a Loder according to the present invention.

DETAILED DESCRIPTION OF PREFERRED EMBODIMENTS

The present invention is of a method, system and composition for local delivery of nucleotide based therapeutic agents, including but not limited to siRNA or shRNA. The agent is preferably delivered, in at least some embodiments, with a "Loder" (Local Drug EluteR). The agents and modifications, design, materials and manufacturing, targets and use, and the insertion methods of Loders are described in greater detail below.

I. Agent: Drugs, Selection of Drugs and Additional Drugs and Modifications Drugs The present invention overcomes the disadvantages of the background art by providing a method, system and composition for local and prolonged delivery of nucleotide based therapeutic agents such as siRNA or shRNA for example. By "nucleotide based therapeutic agent" it is meant any such agent which includes at least one nucleotide, whether natural or non-natural. Non-limiting examples of such agents include but are not limited to any type of RNA interfering (RNAi) agents, single stranded and double stranded, that perform gene knockdown including gene knockdown of message (mRNA) by degradation or translational arrest of the mRNA, inhibition of tRNA and rRNA functions or epigenetic effects; short (also called "small") interfering RNA (siRNA), short hairpin RNA (shRNA), microRNA and non-coding RNA or the like, Morfolinos; Short RNAs activity on DNA, and Dicer-substrate siRNAs (DsiRNAs) (DsiRNA are cleaved by the RNase III class endoribonuclease dicer into 21-23 base duplexes having 2-base 3'-overhangs siRNA), and UsiRNA (UsiRNAs are duplex siRNAs that are modified with non-nucleotide acyclic monomers, termed unlocked nucleobase analogs (UNA), in which the bond between two adjacent carbon atoms of ribose is removed); and Self-delivering RNA (sdRNA) including rxRNA™ (of RXi Therapeutics), siNA (short interfering nucleic acid), and agents inhibiting the pre-mRNA maturation step of polyA tail addition such as the U1 adaptor (IDT Inc.) (The U1 adaptor consists of two parts, a target-gene binding domain and a U'1 domain that attracts and inhibits the cellular splicing apparatus. By combining both capabilities in the same molecule, the U1 adaptor can inhibit the pre-mRNA maturation step of polyA tail addition. Further, the domains of the oligonucleotide are independent so transcript binding and splicing inhibition can be independently optimized and adapted to a wide array of genes). As another example the therapeutic drug could also include microRNA. The microRNA could also induce an upregulation of expression both in cellular and non cellular messages such as the effect of microRNA 122 on Hepatitis C virus (HCV) replication; microRNA122 enhances HCV replication. Also the therapeutic drug could include aptamers, tripel-helix formation, DNAzymes, antisense and ribozyme.

Selection of Drugs and Additional Drugs

The Loder in some embodiments also is covered with an anti-inflammatory coating as in the case upon administration to a site with a high inflammatory response. The anti-inflammatory effect is encountered by using COX-2 inhibition or an anti T cell immunosuppression. In some embodiments related to cases that there is a possibility that the Loder would enter the vascular system the coating is composed of an anti coagulant such as small molecular heparin (for example heparinated PEG).

In some embodiments, the agent is used to treat cancer. Preferably, the agent is selected specifically for a particular type of cancer and is administered locally at the tumor area, in rate that is preferably maintained above the lower threshold of therapeutic effectiveness for prolonged period, and is constant to a certain level to optimize the effective silencing period.

In other embodiments, the agent is used to relieve chronic pain, preventing the accumulation of toxic metabolites, suppress degenerative processes or attenuate inflammation, attenuates apoptosis and necrosis, prevent and/or decrease infection, and inhibit autophagia, dedifferentiation or differentiation of cells, proliferation of cells either malignant or benign, to overcome drug resistance in the case of cancer or infectious diseases; enhance an immune effect or suppress an autoimmune response; act as an adjuvant; control stemness.

Optionally, one or more other types of agents may also additionally be included, apart from but in addition to nucleotide based agents, including but not limited to proteins, including but not limited to growth factors, antibodies, cytokines or their derivatives; peptides, whether linear or circular; peptidomimetics, lectins, carbohydrates and lipids, small molecule drugs, hormones, steroids, anti viral, chemotherapy, radioactive reagents and delivery vehicles, imaging reagents, and/or antibodies either polyclonal or monoclonal human, humanized or otherwise derived.

The additional agent is optionally and preferably selected from the group consisting of anti cancer, chemotherapy, analgesics, anti degenerative, pro-regenerative, antiplatelet drugs, anticoagulant drugs, anti-inflammatory drugs, antireplicate drugs, pro-oxidative, local immune suppression, to generate an immune privileged site, anti-metabolic, anti-infectious including anti viral, anti bacterial, anti fungal and anti parasite, anti-angiogenic, contraceptive, cognitive and combinations of said drugs.

Modifications and Complementary Materials for Nucleotide Based Agents

The drug, as noted above, preferably comprises some type of nucleotide and/or oligonucleotide and/or polynucleotide modifications and conjugation and complexation and more, applied separately and/or in combinations, adjusted for example to reduce degradation by enzymes including RNAse and/or reduce immune stimulations and/or improve cellular up take. Optionally the modifications may be made at one or more locations along the nucleotide based agent. Without wishing to be limited by a single hypothesis, these modifications may optionally be useful for stabilizing the nucleotide based agent and/or for preventing immune stimulation or other immune related effects and/or to reduce unwanted participation in miRNA pathways and to improve cellular up-take and pharmacokinetics. Examples of these modifications include but are not limited to sugar modifications; phosphate linkage modifications; base modifications; conjugation and/or complexation; modifications to the overhangs and termini; and/or modifications to the duplex architecture. A more detailed description of each is given below.

1. Sugar Modifications:

Various modifications to different sugars of the nucleotide agent are possible, many of which have been described and previously tested in the art. Some non-limiting examples of such modifications which may optionally be used with at least some embodiments of the present invention are described herein.

Without wishing to be limited by a single hypothesis, it is believed that the 2'-OH generally is not required for active siRNA. Therefore, the 2' position of the ribose ring is extensively modified, for example to enhance stability against endonucleases and reduce immune response activation. This includes 2'-O-Methylation and 2'-β-methoxyethyl (2'-O-MOE) modification. siRNAs in which 70% of the 2'-OH groups in both strands are converted at random into 2,4-dinitrophenyl ethers (2'-O-DNP) show a variety of improved properties, including higher binding affinity, nuclease resistance and potency. Instead of a hydroxyl, alkoxy or aryloxy substituent, functional siRNAs can contain fluorine at the 2'-position. 2'F-RNA and partial 2'F-RNA modification is tolerated throughout the sense and antisense strands and some fully modified 2'F-RNA siRNAs are also active. An antisense strand made entirely of DNA purines and 2'F-RNA pyrimidines is active. The ring oxygen has also been modified: 4'S-RNA is a high-affinity modification that gives a significant advantage in nuclease stability. The 5'-end of the antisense strand could be modified with a few 4'S-RNA. Combinations of 4'S-RNA with 2'-O-Me and 2'-O-MOE modifications at the termini of both strands is also possible. 4'S-FANA, with modifications at the 2' and 4' positions, has a northern, RNA-like conformation is possible. The drug could optionally be designed with a locked nucleic acid (LNA) or peptide nucleic acid (PNA). LNAs contain a methylene bridge which connects the 2'-O with the 4'-C of the ribose. The methylene bridge "locks" the sugar in the 3'-endo conformation, providing both a significant increase in Tm as well as nuclease resistance.

Figure 1:
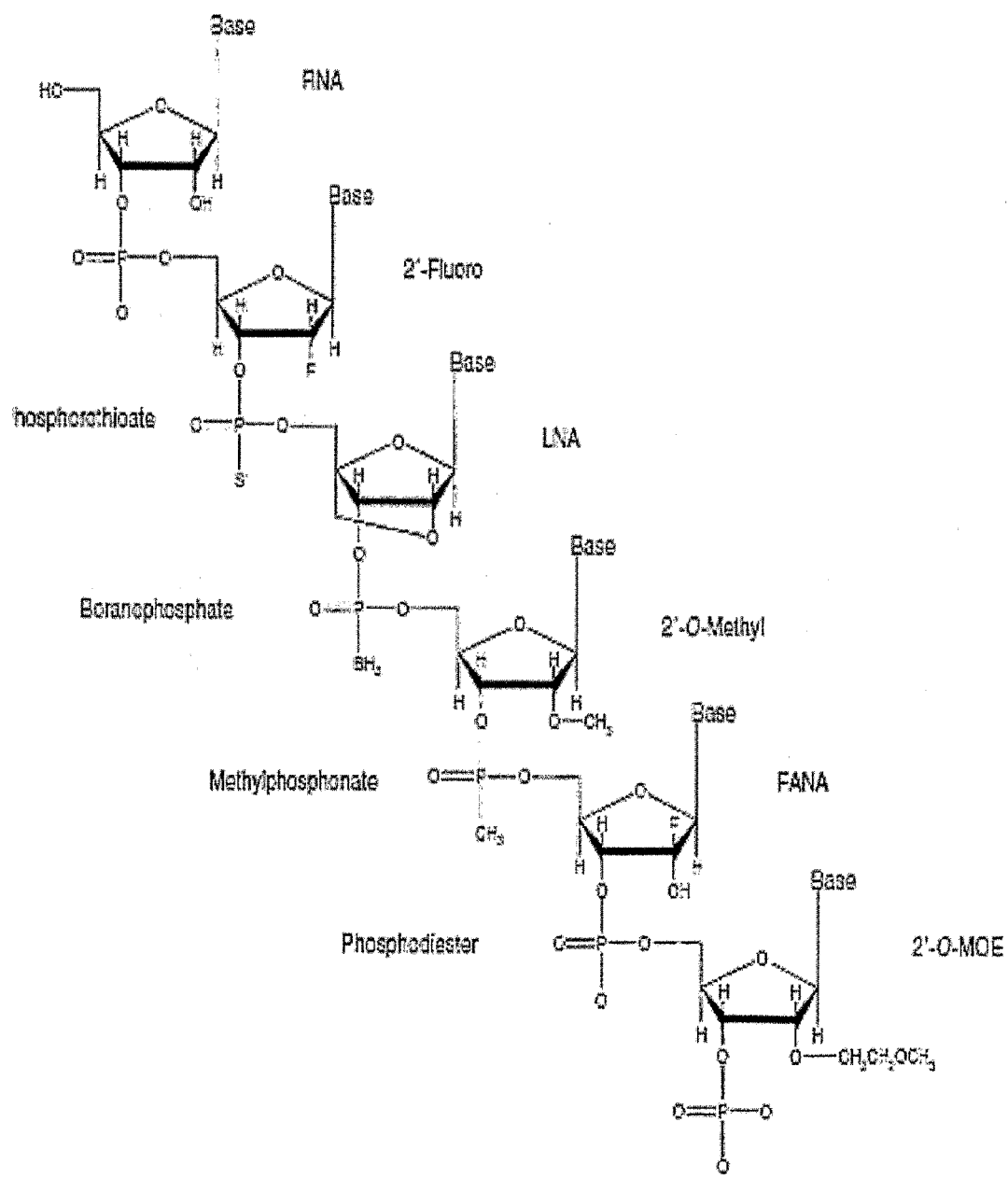
FIG. 1 shows various exemplary modifications for siRNAs and other nucleotide based therapeutic agents.

Modifications to the sugar backbone include but are not limited to 2'-fluoro, LNA (locked nucleic acids), 2'OMe (2'-O-methyl RNA), FANA (2'-deoxy-2'-fluoro-beta-D-arabinonucleic acid), and 2'MOE (2'-O-(2-methoxyethyl)), 4'S RNA. These modifications are shown with regard to FIG. 1. With regard to the use of such modifications, particularly LNAs, care must be taken to ensure that sufficient functionality is retained by the nucleotide based therapeutic agent without problems of toxicity.

Other general types of modifications include but are not limited to 2'-methoxyethoxy nucleotides; 2'-methyl-thioethyl nucleotides, 2'-deoxy-2'-fluoro nucleotides, 2'-deoxy-2'-chloro nucleotides, 2'-azido nucleotides, 2'-O-trifluoromethyl nucleotides, 2'-O-ethyl-trifluoromethoxy nucleotides, 2'-O-difluoromethoxy-ethoxy nucleotides, 4'-thio nucleotides 2'-O-methyl nucleotides; terminal cap moiety of different forms; and so forth.

Some of these modifications are discussed in greater detail below with regard to siRNA, although they could optionally be used for other types of nucleotide based therapeutic agents.

Phosphorothioate (PS) Linkages can be prepared by replacing one of the two nonbridging oxygen atoms in the internucleotide linkage of RNA by a sulfur atom. Boranophosphonate ODNs, the nonbridging phosphodiester oxygen is replaced with an isoelectronic borane (—BH$_3$) moiety. Boranophosphonate siRNAs modified at minimal levels also showed improved stability over unmodified siRNAs against nuclease degradation.

Fluoro and Methyl Linkages.

The siRNA motif consisting of 2'-OMe and 2'-fluoro nucleotides has enhanced plasma stability and increased in vivo potency. The 2'-OMe sugar modification retains the canonical right-handed A-form helical geometry, which is required for siRNA activity. This modification has also been shown to increase the nuclease resistance of ODNs and siRNA duplexes.

Locked Nucleic Acid.

Locked nucleic acid (LNA), also referred to as inaccessible RNA, is a family of conformationally locked nucleotide analogs that displays unprecedented hybridization affinity toward complementary DNA and RNA. LNA also contains a methylene bridge connecting the 2' oxygen with the 4' carbon of the ribose ring. This bridge locks the ribose ring in the 3'-endo conformation characteristic of RNA. LNA has been shown to be compatible with siRNA intracellular machinery, preserving molecule integrity while offering several improvements that are relevant to the development of siRNA technology.

2. Phosphate Linkage Modifications:

Several variations on the phosphodiester linkage are also accepted by the RNAi machinery. Also Boranophosphate siRNAs provide a significant increase in nuclease stability. A 2',5'-linkage, 2',5'-DNA or 2',5'-RNA, amide-linked 2',5', can substitute for the native 3',5' linkage. A nonionic amide linkage in the 3'-overhangs of siRNA duplexes, also methylphosphonate.

3. Base Modifications:

Modified bases that stabilize A-U base pairs (5-Br-Ura and 5-I-Ura instead of uracil, and diaminopurine instead of adenine). This includes 4-Thiouracil has also been used, 2-Thiouracil and the C-linked base pseudouracil. 5-Methylation of pyrimidines (i.e. use of T and 5-Me-C instead of U and C) in conjunction with sugar modifications such as DNA, 2'F-ANA and LNA. A difluorotoluoyl base, which has the same shape as thymine but cannot form hydrogen bonds, can replace uracil at single positions throughout an siRNA duplex. A nonaromatic base, dihydrouracil, can also be used, but because it cannot contribute to base stacking it lowers the binding affinity of the duplex and is best placed at the 5'-end of the duplex, as defined by the antisense strand.

Specific illustrative examples of modified bases include but are not limited to deoxyinosine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science and Engineering, pages 858-859, Kroschwitz, J. L, ed. John Wiley and Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993, all of which are hereby incorporated by reference as if fully set forth herein.

4. Conjugation and/or Complexation

In some embodiments of the present invention, the nucleotide based agents may optionally be modified and/or may optionally feature one or more complementary materials. Such one or more complementary materials do not necessary change the chemical composition of the nucleotide based agent through a covalent bond. The drug could optionally be conjugated to lipid moieties such as cholesterol for example to improve penetration. More generally, conjugation with membrane-penetrating peptides and lipophilic groups including steroids and lipids could improve the drug delivery.

The drug could optionally be mixed and/or complexed with polycations and/or cationic peptides and/or natural polymers including Spermin, Phosphatidylethanolamine (named PE or Cephalin) including L-α-Cephalin, DOPE and/or polyethyleneimines (PEI) and its derivatives including jetPEI, and/or Lipofectamine/RANiMAX, RNotion, Silencer, Gene Eraser, siPORT, siFECTOR, TriFECTIn, BlOCK-it, Oligofectamine, TransIT-siQUEST, TransIt-TKO, Dreama-Fect, for example to improve stability and/or enhance cellular uptake; and/or additives, plasticizer and pigments. The drug could optionally be mixed with bovine serum albumin (BSA), Mannitol, cell membrane and endosomal disrupting molecules.

With regard to complementary materials, such one or more complementary materials may optionally include any material that is suitable for a delivery carrier, preferably a non-viral delivery carrier, including but not limited to cationic lipids and polymers. Non-limiting examples of cationic lipids include cardiolipin analogs and lipiodol. Non-limiting examples of polymers include branched peptides, such as branched histidine-lysine (HK) peptides for example, or polymers such as polyethylenimine (PEI), protease treated collagen (atelocollagen), chitosan or oligofectamine, and/or other natural polymers including spermin and cephalin (phosphatidylethanolamine), for example.

US Patent Application No. 20080213377, hereby incorporated by reference as if fully set forth herein, describes various exemplary cationic polymers which include polyethylenimine (PEI), polylysine (PLL), polyarginine (PLA), polyvinylpyrrolidone (PVP), chitosan, protamine, polyphosphates, polyphosphoesters (see U.S. Pat. No. 6,852,709, which is also hereby incorporated by reference as if fully set forth herein), poly(N-isopropylacrylamide), etc. Certain of these polymers comprise primary amine groups, imine groups, guanidine groups, and/or imidazole groups. Some examples include poly(beta-amino ester) (PAE) polymers (such as those described in U.S. Pat. No. 6,998,115 and U.S. Patent Publication 2004/0071654; both of which are hereby incorporated by reference as if fully set forth herein). The cationic polymer may be linear or branched. Blends, copolymers, and modified cationic polymers can be used. In certain embodiments, a cationic polymer having a molecular weight of at least about 25 kD is used. In some embodiments, deacylated PEI is used. For example, residual N-acyl moieties can be removed from commercially available PEI, or PEI can be synthesized, e.g., by acid-catalyzed hydrolysis of poly(2-ethyl-2-oxazoline), to yield the pure polycations.

In addition, the delivery carrier may optionally feature any ligand or other molecular structure which increases targeting to a particular cell type or environment, and/or which increases "stickiness" to the cell type or environment, for example in order to increase the likelihood of penetration to the desired cell type or a reduced chance of leaving the desired cell type or environment before penetration thereto.

Some non-limiting examples of conjugations are described in greater detail below specifically with regard to siRNA, although they could optionally be applied to any type of nucleotide based therapeutic agent as described herein.

Bioconjugation:

Bioconjugation of one or both strands of siRNAs with lipids and polymers is often desirable to (1) further increase their thermodynamic and nuclease stability, (2) improve the biodistribution and pharmacokinetic profiles of siRNAs, and (3) target them to specific cell types.

Lipid Conjugation.

Conjugation with lipids may enhance siRNA uptake via receptor-mediated endocytosis or by an increased membrane permeability of the otherwise negatively charged RNA. Conjugation of nucleic acids with cholesterol has been demonstrated to enhance cellular uptake in cell culture and hepatic deposition after systemic administration.

Peptide Conjugation.

Protein transduction domains (PTDs) offer an alternative to the traditional methods of siRNA delivery. PTDs are short amino acid sequences that are able to interact with the plasma membrane in a way that leads to a highly efficient uptake into the cytoplasm.

Non-limiting examples of types of conjugations include cholesterol and/or palmitate conjugations, α-tocopherol (Vitamin-E) conjugations, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374 (hereby incorporated by reference as if fully set forth herein), MEA-dynamic polyconjugate particles and multi-component polymer conjugations.

Multi-component polymer systems may optionally feature, for example, a membrane-active polymer to which the nucleotide based therapeutic agent is covalently coupled, for example via a disulfide bond, with one or more other polymers such as a polymer for charge masking (PEG, for example) and/or targeting. These latter polymers are preferably conjugated through labile bonds that are cleaved upon entry to the cell. MEA-dynamic polyconjugate particles are made of the same or similar materials but in particle form.

5. Modifications to the Overhangs and Termini:

siRNA in its primary form may optionally feature a plurality of nucleotides in 3'-overhangs. Overhang modification may optionally include deoxy units used in the 3' overhangs and/or blunt-ended duplexes resistant to 3'-exonucleases. The termini of the strands can also optionally be modified, for example through chemical phosphorylation of the 5'-end of the antisense strand and/or 5'-phosphorylation of the sense strand. Optionally, various groups can be conjugated to the ends of siRNA duplexes, especially the termini of the sense strand. These groups can include an inverted abasic end cap. Also, including 5-8 dA and dT units on the 3'-ends of the strands can lead to reversible concatemerization through these sticky ends, which in turn leads to higher efficiency delivery in complex with for example PEI. Fluorescein is optionally conjugated to any of the termini except the 3'-end of the antisense strand.

6. Modifications to the Duplex Architecture:

It has been shown that an siRNA could also be made of made of three strands (an intact antisense strand with two sense strands), rather than only two strands, and that the use of three strands can reduce off-target effects and increase potency; the resulting duplex is termed small internally segmented interfering RNA (sisiRNA). Functional siRNA can also be made from just one strand, in one of the various ways. Hairpin-type duplexes, made from a single strand, can be introduced exogenously or expressed within a cell. Closing the other end of the hairpin results in a dumbbell or nanocircle which retains RNAi activity while providing complete protection from exonucleases. A single-stranded antisense RNA (which does not fold into a duplex at all) has been shown to enter the RNAi pathway, with potency approaching that of the duplex siRNA in some cases.

The length of an siRNA duplex can also be changed. Most synthetic duplexes are 19-21 bp in length, mimicking the natural products of the Dicer enzyme. However, increasing the length of an siRNA duplex makes it a substrate for Dicer and has been found to increase its potency. Optionally and preferably the length of the molecule is below 30 nt, to avoid triggering the interferon response.

II. Design

As described herein, according to at least some embodiments of the present invention, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation as used herein. The drug delivery system is preferably implemented as a "Loder" as described herein.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 mm^3 to 1000 mm^3, as required by the volume for the agent load. The Loder may optionally be larger, for example when incorporated with a device whose size is determined by functionality, for example and without limitation, a knee joint, an intrauterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described herein is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

As described above, the composition preferably features one or more polymers, which are optionally arranged in a substrate, such as a matrix for example. Additionally or alternatively, optionally the composition is based on an assembly of tiny polymeric fibers encapsulating drug. The fibers typically are of micro and nano scale diameter 10 nm-10,000 nm, and are manufactured preferably by electrospinning methods, including methods described in (7-10); all references cited herein are hereby incorporated by reference as if fully set forth herein Optionally and more preferably, drug release is provided at a concentration sufficient to achieve a therapeutic effect for a period of time sufficient for extended release. The effective release period optionally, but not limited to, lasts within one to four months, where some more embodiments are designed for short periods of a few days, or other embodiments of periods longer than four months.

The polymeric substrate, such as a matrix for example, is made of a polymer film/cast, and/or, polymer fiber bundle, and/or, in cases for example less sensitive to high temperatures, polymer cast and/or polymer mold, where the polymer, or plurality of polymers, and the drug or plurality of drugs have been dissolved separately or altogether, or elsewhere combined for example when the drug is lyophilized, and stirred or mixed else wise, or for example the two phases combined in a dual layer fiber as described later, as long as the entire process have been arranged in room temperature or slightly elevated temperatures, but preferably not higher than 65° C. (or any other temperature well tolerated by the drug or plurality of drugs).

In another embodiment the polymeric substrate comprises and/or incorporates a fibrous substrate made of one or more of the methods including fiber molding, fiber electrospinning, melt spinning, dry spinning and wet spinning having fiber diameters in the range of from about 10 up to about 10000 nanometers. The substrate may optionally form a matrix.

In another embodiment the polymeric substrate is made in a multi layer design, for example a barrel model (outer coat), where, for example, the inner main body is of very high Polymer:Drug load ratio, for example ~2:1, as an example the polymer is PLGA 50:50, and the outer thin layer is for example a pure PLA.

In another embodiment the polymeric substrate is associated with non-polymeric material, including metals, for example as in osmotic pump devices (such as Viadur).

The delivery carrier and the nucleotide based therapeutic agent may optionally be condensed into a tiny nanoparticle with size of only about ~50-150 nm, which increases the efficiency of cellular uptake of the nucleotide based therapeutic agent through the endocytosis process. Other possible carrier structures include but are not limited to liposomes and micelles. Nanoparticles may optionally be based on materials such as cyclodextrins or transferrin-cyclodextrin combinations for example, in addition to or in replacement for the above described carrier materials. In such a case for example the polymeric substrate incorporates a large number of such nanoparticles.

III. The Materials of the Drug Delivery System, Preferably as a Loder, and Manufacturing 3.1 Materials As described above, the Loder preferably comprises one or more polymers, more preferably selected for sustained release. The polymer optionally comprises a monomer selected from the group consisting of a glycolide and glycolic acid, lactide, dioxanone, caprolactone, trimethylene carbonate, ethylene glycol, ethylene oxide amidoamine, alkylcyanoacrylate, 3-hydroxybutanoic acid, organophosphazene, L-glutamic acid, ethyleneimine, propylene imine and lysine.

The polymer optionally comprises a biostable and/or biodegradable and/or bioabsorbable polymer, including linear aliphatic polyester, including natural polymers polysaccharides including starch, cellulose; protein including gelatin, wool; polyesters (polyhdroxyalkanoates PHAs) and other including lignin, shellac, natural rubber, and synthesized biodegradable polymers, including polyglycolide (PGA), polylactic acid (also named polylactide, PLA) and its copolymers including all forms of the copolymer poly(glycolide-co-lactide) (PLGA), Polycaprolactone (PCL), poly(anhydride-co-imides), poly(ethylene glycol) (PEG), polyvinyl alcohols (PVOH, PVA, or PVAL), esters, polyamide esters, polyanhydrides and polyalkylene esters, Poly(alkylcyanoacrylate), Poly(3-hydroxybutanoic acid), Poly(organophosphazene), Poly(ethylene glycol), Poly(ethylene oxide), Poly(amidoamine), Poly(L-glutamic acid), Polyethylene (PE), Polyethylene Imine (PEI), Poly(propylene imine), and its groups, Alginate, polysaccharides, including mixtures of them, and copolymers of them and their derivatives.

According to still other embodiments, the polymer optionally is selected from a group consisting of the following polymers: Fibrin, Collagen, Chitosan, Gelatin, Hyaluronan, Polyvinyl acetate (PVA or PVAc), Silicon, PEG (PEO), Polyorthoesters, Poly(dioxanone), Poly(anhydrides), Poly(trimethylene carbonate), Polyphosphazenes and mixtures and/or copolymers thereof.

According to other embodiments, the composition is delivered in a device constructed of a biocompatible metallic material selected from the group stainless steel metals, cobalt chromium metals, nickel titanium metals and magnesium metals, or alloys or composites thereof.

3.2 Manufacturing

In an embodiment the drug, either dissolved or lyophilized, is mixed with a polymer that is dissolved in a solvent, and the drug and the polymer are stirred and later dried to form a polymeric film (cast), where the entire process is carried out for example in room temperature. Examples 1.1 and 1.2 describe non-limiting examples thereof.

In another embodiment the drug is embedded in the polymer and a single fiber is electrospun. In another embodiment the electrospun fiber is hollow (for example coaxial fiber as described in patent application (11)) and the drug is preferably embedded during the electrospinning process to the inner fiber by two-syringe (two component) electrospinning method.

In other examples manufacturing methods include but are not limited to Melt spinning (typically for large diameter range 10 um-50 um); and Melt blowing (1-20 um). Other embodiments include but are not limited to polymeric "sponge" and fiber mat. Manufacturing methods of controlled release systems enabling prolonged and constant diffusion rate for extended periods may also optionally be incorporated.

In other examples the selected polymer(s) is from a group of bio-compatible (and usually also biostable) elastomers, including silicon and PVA. Such polymers can support devices including intravaginal devices, preferably for prevention of infections, for controlled release of siRNA, including anti-HIV siRNA with or without other compounds including hormones. Typically the preparation of the polymer-siRNA mixed device is done at room temperature, for example using room temperature vulcanizing (RTV) methods. Typically a poly dimethylSiloxane (an example of an RTV silicone material) is mixed with a lyophilized siRNA, the mixture is placed into a (e.g. polypropylene) mold and vulcanized for 24 h at room temperature.

Room temperature vulcanizing (RTV) silicone material typically features one or more reactive oil base polymers combined with one or more minerals to strengthen the vulcanized material. There are two types of room temperature vulcanizing silicone: one component (RTV-1) and two component (RTV-2) systems.

RTV-1 materials harden directly due to humidity in the atmosphere, as a single component, without the addition of another product to induce curing. The curing process begins on the outer surface and progresses through to its core. The product is packed in airtight cartridges and is either in a fluid or paste form. The above described example for use with a nucleotide based agent, such as lyophilized siRNA, relates to a one component or RTV-1 material.

RTV-2 materials feature two components that cure at room temperature upon being mixed, thereby hardening to a solid elastomer, a gel, or a flexible foam.

Optionally the drug-polymer substrate, such as a matrix for example, is attached to additional device and/or scaffolding materials, including metallic-scaffold and/or additional polymer scaffold that is not compounding drugs, and/or materials enhancing visibility including x-ray visibility and/or ultrasonic, and/or imaging, and/or devices including IUDs, IVRs, Stents.

IV. The Targets and Use, and Methods of Insertion 4.1 The Target and Use

According to some embodiments of the present invention, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle. The site for local delivery also may optionally include sites enabling performing preventive activities including pregnancy, prevention of infection and aging.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder):

1. brain at degenerative sites like in Parkinson or Alzheimer disease at the basal ganglia, white and gray matter.
2. spine as in the case of amyotrophic lateral sclerosis (ALS)
3. uterine cervix to prevent HPV infection
4. active and chronic inflammatory joints
5. dermis as in the case of psoriasis
6. sympathetic and sensoric nervous sites for analgesic effect
7. Intra osseous implantation
8. acute and chronic infection sites
9. Intra vaginal
10. Inner ear—auditory system, labyrinth of the inner ear, vestibular system
11. Intra tracheal
12. Intra-cardiac; coronary, epicardiac
13. urinary bladder
14. biliary system
15. parenchymal tissue including and not limited to the kidney, liver, spleen
16. lymph nodes
17. salivary glands
18. dental gums
19. Intra-articular (into joints)

20. Intra-ocular
21. Brain tissue
22. Brain ventricles
23. Cavities, including abdominal cavity (for example but without limitation, for ovary cancer)
24. Intra esophageal
25. Intra rectal Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments, the drug preferably comprises a gene silencing biological RNAi drug, for example for localized cancer cases in breast, pancreas, brain, kidney, bladder, lung, and prostate as described below. Moreover, many drugs other than siRNA are applicable to be encapsulated in Loder, and can be used in association with this invention, as long as such drugs can be encapsulated with the Loder substrate, such as a matrix for example. Such drugs include approved drugs that are delivered today by methods other than of this invention, including Amphotericin B for fungal infection; antibiotics such as in osteomyelitis; pain killers such as narcotics; anti degenerative such as in Alzheimer or Parkinson diseases in a Loder implanted in the vicinity of the spine in the case of back pain.

For example, for specific applications such as prevention of growth or regrowth of smooth muscle cells (that are injured during a stenting procedure and as a result tend to proliferate), the drug may optionally be siRNA that silence smooth muscle cells, including H19 silencing, or a drug selected from the group consisting of taxol, rapamycin and rapamycin-analogs. In such cases the Loder is preferably either a Drug Eluting Stent (DES), with prolonged release at constant rate, or a dedicated device that is implanted separately, in association to the stent.

As another example of a specific application, neuro and muscular degenerative diseases develop due to abnormal gene expression. Local delivery of silencing RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately.

As yet another example of a specific application, psychiatric and cognitive disorders are treated with gene modifiers. Gene knockdown with silencing RNA is a treatment option. Loders locally delivering nucleotide based agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites.

As another example of a specific application, silencing of innate and/or adaptive immune mediators at local sites enables the prevention of organ transplant rejection. Local delivery of silencing RNAs and immunomodulating reagents with the Loder implanted into the transplanted organ and/or the implanted site renders local immune suppression by repelling immune cells such as CD8 activated against the transplanted organ.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

Method of Insertion

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Optionally, the dimensions of the drug delivery system (optionally including the device and composition) are tailored for implantation via brachytherapy procedure and the design is of cylindrical body, for example optionally of 5 mm length and 1.1 mm diameter.

Optionally, the dimensions of the insertion (implantation) system for inserting the Loder (optionally including the device and composition) are tailored for implantation via biopsy needles, for example having a diameter in the range of from about 17 to about 19 gauge.

According to some embodiments, the composition is attached to a stent and/or graft and/or to a metallic and/or to a polymeric device, which is optionally of a tubular designed to be associated and/or expended against vessel walls and/or tubular ducts in the mammalian body, including arteries, veins, gastro-intestinal, respiratory systems, and the composition (optionally with a device) is implanted using stent implantation techniques, including balloon expandable stents and/or self expandable stents.

The device containing the composition is optionally covered with an anti-inflammatory, including anti-inflammatory effect encountered by using COX-2 inhibition or anti T cell immunosuppression, and/or with an anti coagulant including small molecular heparin.

Without wishing to be limited in any way, the below description centers around the implementation of the present invention for treatment of particular diseases. Non-limiting examples of some of the types of cancers and other diseases that may optionally and preferably be treated with the present invention are given below.

Breast Cancer

The tumor typically is localized and concentrated in ~10-50 mm area, which makes it proper candidate to localized therapeutic treatment. Estimated new cases and deaths from breast cancer in the United States in 2008: New cases: 182,460 (female); 1,990 (male); Deaths: 40,480 (female); 450 (male). Infiltrating or invasive ductal cancer is the most common breast cancer histologic type and comprises 70% to 80% of all cases. HER2-positive tumors, is a particularly aggressive form of cancer that affects approximately 20 percent to 25 percent of breast cancer patients. Two agents, trastuzumab (Herceptin) and lapatinib (Tykerb), have already been approved by the U.S. Food and Drug Administration for use for treatment of HER2-positive breast cancer.

Ductal carcinoma in situ (DCIS) is a noninvasive condition. DCIS accounted for about 18% of all newly diagnosed invasive plus noninvasive breast tumors in the United States—but the % is increasing. Very few cases of DCIS present as a palpable mass; 80% are diagnosed by mammography alone. Treatment Options for Patients with DCIS (12): 1. Breast-conserving surgery and radiation therapy with or without tamoxifen. 2. Total mastectomy with or without tamoxifen. 3. Breast-conserving surgery without radiation therapy. Present data are insufficient to recommend CA 15-3 or CA 27.29 for screening, diagnosis, and staging.

Pancreatic Cancer:

Pancreatic cancer is an aggressive tumor which is usually diagnosed at late stage. The current estimated of new cases and deaths from pancreatic cancer in the United States in 2008 is 37,680 for new cases and 34,290 for deaths. Carcinoma of the pancreas has had a markedly increased incidence during the past several decades and ranks as the fourth leading cause of cancer death in the United States. Despite the high mortality rate associated with pancreatic cancer, its etiology is poorly understood. Cancer of the exocrine pancreas is rarely curable and has an overall survival (OS) rate of less than 4%. The highest cure rate occurs if the tumor is truly localized to the pancreas; however, this stage of the disease accounts for fewer than 20% of cases. For those patients with localized disease and small cancers (<2 cm) with no lymph node metastases and no extension beyond the capsule of the pancreas, complete surgical resection can yield actuarial 5-year survival rates of 18% to 24% Improvements in imaging technology, including spiral computed tomographic scans, magnetic resonance imaging scans, positron emission tomographic scans, endoscopic ultrasound examination, and laparoscopic staging aids in the diagnosis and the identification of patients with disease that is not amenable to resection. No tumor-specific markers exist for pancreatic cancer; markers such as serum CA 19-9 have low specificity. Most patients with pancreatic cancer will have an elevated CA 19-9 at diagnosis. Following or during definitive therapy, the increase of CA 19-9 levels may identify patients with progressive tumor growth. The presence of a normal CA 19-9, however, does not preclude recurrence. Complete surgical resection is the only potentially curative option for pancreatic cancer. However, most patients have advanced/metastatic disease at the time of diagnosis, or will relapse after surgery. Systemic chemotherapy is only palliative. Gemcitabine-based therapy is an acceptable standard for unresectable locally advanced/metastatic pancreatic cancer, but average median survival is only 6 months.

Pancreatic cancer is the second most frequent gastrointestinal malignancy and carries a dismal prognosis. The current standard of care includes resection, if possible, as well as systemic chemoradiation therapy. Endoscopic ultrasound (EUS) is an established technique for the diagnosis and staging of pancreatic adenocarcinoma. Interventional EUS via fine needle injection (FNI) for the treatment of pancreatic cancer is a rapidly expanding field.

Among the Loder's many advantages for treatment of pancreatic cancer include but are not limited to its size, approximation to tumor microenvironment, and the ability to deliver a specific drug or combination of drugs for an extended period of time.

Background Information for Prostate Cancer:

The current estimated of new cases and deaths from prostate cancer in the United States in 2008 is 186,320 for new cases and 28,660 for deaths. Since the early 1980s, there are 3 primary treatment strategies for clinically localized prostate cancer: 1. Radical prostatectomy. 2. Definitive radiation therapy. 3. Watchful waiting. A randomized trial comparing radical prostatectomy to watchful waiting in men with early-stage disease in the pre-PSA screening era (clinical stages T1b, T1c, or T2) showed a statistically significant difference in overall survival OS at 10 years. After 10 years, the difference in OS was approximately 73% versus 68%; absolute difference 5.0%; relative risk of death 0.74 (95% confidence interval, 0.56-0.99). This benefit was restricted to men younger than 65 years at the time of surgery (P=0.01 in a planned subset analysis of the effect of age on treatment efficacy). Results from the Prostate Intervention Versus Observation Trial (PIVOT) in the United States, an ongoing randomized trial that compared radical prostatectomy with watchful waiting, have not been reported. The PIVOT uses overall mortality as its primary endpoint (13, 14).

Prostate Brachytherapy:

Brachytherapy is a minimally invasive procedure where tiny permanent radioactive seeds (5 mm×1.1 mm in many cases) are implanted into the prostate where they irradiate the cancer from inside the gland (15). The implanted seeds are small enough that they will not be felt by the patient. Depending on circumstances, either radioactive Iodine (I-125) or palladium (Pd-103) are used. Brachytherapy is also referred to as interstitial radiation therapy or seed implant therapy. Before the seeds are implanted, the patient receives anesthesia. Needles containing the seeds are then inserted through the skin of the perineum (the area between the scrotum and anus) using ultrasound guidance. The seeds remain in the prostate, where the radioactive material gives off localized radiation for a number of months to destroy the prostate cancer. In a similar way, a Loder may optionally be administered through a brachytherapy procedure; for such a situation, preferably the Loder features a cylindrical body of 5 mm length and 1.1 mm diameter.

HIV Transmission and Prevention Thereof:

After 25 years into the AIDS pandemic condoms still remains the leading means for preventing sexual transmission of HIV, obviously a poor solution as are used inconsistently. Vaginal microbicides offer a woman-controlled solution potentially with higher acceptability. However, so far Large-scale HIV prevention clinical trial results have been disappointing: nonxoynol-9, cellulose sulfate, and Savvy showed a potential increase in HIV transmission; Carraguard and BufferGel showed no effect. Only PRO 2000 demonstrated a trend toward reduction in HIV transmission. These gels are applied temporally close to intercourse, but acceptability of products used immediately before intercourse (condom, spermicide and so forth) is low, compared with products indicated for use noncoitally such as oral contraceptive. Also, none of the recombinant proteins offered as microbicides are currently being evaluated clinically.

Evidences that circumcision can reduce sexual HIV transmission encouraged large scale surgical interventions in some countries.

The majority of microbicide agents in clinical development are HIV specific, however 340 million people acquire annually one of the four primary curable sexually transmitted infections (STIs), and unknown numbers acquire chronic viral and bacterial infections. In addition to causing significant morbidity on their own, many non-HIV STIs are cofactors for transmission of HIV.

Design Implant Device for these Applications and Also for Female Gynecological Applications In some embodiments, the Loder is preferably a small implant of typical dimensions of a few mm, as described in some examples, and of shapes including but limited to cubic, tube, ring, thin fiber, or flat patch. A Loder includes a polymeric substrate, such as a matrix for example, encapsulating drug or a plurality of drugs, and is designed to be inserted and permanently or semi-permanently implemented into a mammalian tissue/body and to release drug locally, direct to the extracellular matrix of the target diseased site or at site approximating the diseased tissue.

The preferred effective radius of drug diffused from the Loder is <2~3 cm for such applications as treatment of tumors.

In another exemplary embodiment the Loder is associated with, or is part of, a device that is inserted to the body, including devices such as IUD, vaginal rings and stents. The drug is released to the diseased site, at a controlled and prolonged pace. In one preferred embodiment release preferably lasts effectively for at least 4 weeks.

For all applications, the drug load and drug release rate are optimized per the specific application and drug type.

EXAMPLES

This Section provides a number of illustrative, non-limiting examples regarding actual and proposed preparation and use of various Loder embodiments according to the present invention. When the selected polymer is bio-degradable, the drug is released or partly released by bulk erosion. Drug release by diffusion also takes place and in some embodiments could be dominant.

At the surface of the Loder the diffusion is in most cases to the ECM and the Loder design is optimized, in some typical cases specifically when diffusion is the main mode of release, to approach diffusion coefficient in the range 0.1-10×10-7 cm^2/sec. The Loder is designed preferably so that the internal part of the Loder functions as drug reservoir, which practically is not affected by the surroundings for a long period, ranges from a week to a few months, and the concentration gradient at the surface is maintained effectively constant, and therefore the diffusion rate is effectively constant (namely "zero mode" diffusion is practically achieved).

The Loder design, in some embodiments, is based on a polymeric substrate, such as a matrix for example, encompassing the drug. The selection of polymer type and substrate, such as a matrix for example, is preferably tailored per requirements including the total period of release, dimensions of Loder and dimensions of the target, environment parameters such as pH and more. Polymer selection preferably includes biostable, biodegradable and bioabsorbable polymeric materials that are selected to be biocompatible and meet manufacturing requirements, such as dissolving in permitted solutions. The polymeric substrate, such as a matrix for example, can be made using molding, film-casting, and the like. The Loder could be built by a single polymer such as PCL, but many variations of co-polymers and more are possible.

One non-limiting example enabling high flexibility is the co-polymerization of PLA and PGA in different ratios, yielding biodegradable co-polymer, where ratios at the two ends greater than 75:25 but at least 25:75 enable bio-degradation longer than at least about 10 weeks, while the ratio of 50:50 yields stability for typically about 8 weeks. Higher molecule weights will also maintain stability for extended periods. Another example is tri-block PLA-PCL-PLA. The polymer, or plurality of polymers, and the drug or plurality of drugs, are mixed for example as described in Examples 1.1, 1.2 and/or 2. The manufacturing process including the drug is preferably performed at room temperature or slightly elevated temperatures, but preferably not higher than 60 C (or any required temperature to maintain drug stability and functionality).

In some embodiments the Loder includes additional scaffolding materials that are not part of the drug-polymer substrate, such as a matrix for example, such as metallic-scaffold or additional polymers, and materials to enhance visibility including x-ray visibility and ultrasonic, and imaging.

The Loder is preferably implanted in the ECM at body conditions without further material(s) and/or adjustments. In other embodiments, alternatively injection of material to the ECM at the vicinity of the Loder during or after the Loder implementation is performed to affect local pH or other biological factors affecting the diffusion of the drug in the ECM and cellular up-take.

Example 1

Loder Preparation

This Example provides two exemplary, illustrative non-limiting methods for preparing Loders according to various embodiments of the present invention. The first Example, Example 1.1, is a specific protocol relating to preparation of a Loder featuring a polymer film, according to some embodiments of the present invention. Unless otherwise indicated, Loders tested in various in vitro and in vivo experiments below were prepared according to this Example.

Example 1.2 relates to another method of preparing a Loder according to some embodiments of the present invention, by polymer cast.

Example 1.1

Protocol for Preparation of Loder by Polymer Film 1. 10% Mannitol was dissolved in water, until a clear solution was achieved.
2. siRNA was dissolved in aqueous solution and added to Mannitol (in the following examples siRNA is one or more of
   siGFP,—siRNA against Green Fluorescent Protein
   siLUC—siRNA against luciferase
   siK-Ras,—siRNA against K-Ras
   si-KRASG12D (siK-Ras$^{mt}$)—siRNA against K-Ras mutated,) and complexed siRNA with transfection reagent (TR), in general a cationic polymer, with stirring to obtain a complex. Although various cationic polymers are described herein, for the below examples PEI was used unless indicated otherwise. Other transfection reagents that were successfully used experimentally include Lipofectamine 2000 (for in-vitro only) Spermine, jetPEI, L-α-Cephalin, DOPE).
3. The products of stages 1 and 2 were combined with stirring.
4. The resultant material was then frozen in liquid nitrogen and lyophilized for 24 h
5. The particle size and zeta potential was then tested. [Results not provided here]
6. In parallel, X % (in the Examples herein 10%<X<35%) PLGA (50:50) Mw: 40,000-75,000) was dissolved in Chloroform and stirred for 1 hour.
7. The PLGA 50:50 solution was poured onto the siRNE/TR/Mannitol in fractions and stirred until homogenization.

8. The resultant material was poured onto Petri dish covered with Teflon (D=30 mm; 21 mm; 15 mm. # of loders: (D/d)^2 d=loder diameter)).
9. The material was dried in the hood (168 h), to obtain a film.
10. The film was punched to obtain Loders.

Example 1.2

Preparation of Loder by Polymer Cast

In a more generalized example the Loder is built mainly of a cast substrate, such as a matrix for example, where the die for casting is preferably designed according to the specific Loder embodiment. For example in a non-degradable Loder featuring a ring made of Silicon, for example to be used as IVR, the die is preferably of a ring shape. In another general case, the drug release mechanism in addition to diffusion, significantly and sometimes mainly is degradation of the polymer associating with release of drug. The selection of the biodegradable polymer, including combinations such as copolymer and tri-block, and the proper molecular weight, is mainly based on the degradation mode, specifically surface degradation vs. bulk, where bulk is preferable here to achieve more stable release, and the typical degradation half time is longer then the required effective therapeutic period. Half time measurements are usually performed, and so cited in the literature, for matrices of larger volume, and matrices having a smaller surface/volume ratio than for Loders. Therefore it is preferable to select polymers of "literature value" degradation time longer then the value required for Loders. For example, in (19) the tri-block PLA-PCL-PLA film of 10×10× 0.4 mm is stable for 20 weeks, because it is hydrophobic, then degrades rapidly in the successive 8 weeks, then degrades much slower. In this example the Tri-block comprises hydrophilic component, the drug, which drives swelling at the first stages and thereby accelerates drug release. The achieved drug release curve is more gradual rather than (semi) step. As described in Example 1.1 an additive could be added to reduce drug-polymer hydrophilic-hydrophobic interaction and/or swelling (e.g. Mannitol).

For the following non-limiting example, DL-PLG 75/25 was selected for surface diffusion and polymer degradation. The parameters for dissolution were selected to be $t\_½$-4 month, to achieve a drug release period of ~10 weeks, as follows: Dissolving 10 g of DLPLG 75/25 (Ester end groups, IV ~0.7 dL/g) LakeShore Biomaterials in 90 g Methylene Chloride to receive 10:90 w/w solution, in room temperature, until full dissolution (~60-120 min). Then 1 g lyophilized siRNA is added with continuous stirring (vortex, or gentle magnetic), which is continued at room temperature to for about 110 min until receiving a homogeneous solution. In other embodiments the siRNA is dissolved first for example in water, to get a suspension, at 1:10 w/w ratio additionally with BSA 1:10 w/w, and then the siRNA solution is added to the DLPLG solution.

The Polymer-siRNA solution is poured into a glass-made die of cylindrical shape D=12 cm, H=4 cm, (optionally including vortexing), for solvent evaporation. The solvent is evaporated until drying is achieved (~100 h) at room temperature, and then the result cast film optionally is transferred to a vacuum chamber for further evaporation at 30 C, for 20 min. The resultant film is larger compared to Example 1.1 and more suitable for handling and additional processes such as spraying of a thin "top coat" polymeric envelope to avoid initial burst in release (for a bi-layer design of the Loder). The final cast is mechanically cut by a dedicated tubular die/punch, or a dedicated grid-like cutter, resulting with cylindrical Loder of 5 mm length, 1.1 mm diameter, to reach the implant dimension equivalent to radioactive seeds used in Brachytherapy, and total weight that is optionally and preferably optimized to meet the following ratio ~5.5 mg, siRNA/DLPLG ~0.5 mg/5 mg (although such a ratio is not mandatory).

Example 2

Preparation of Fiberspun-Based Loder

Another approach for slow release is achieved by trapping the drug within non-degradable polymeric nanofiber (or degradable polymer of $T\_½$ typically longer than ~4 month). At first a film made of mat of coaxial nanofibers is manufactured by co-axial electrospinning, as described below. Then, in the same manner described in example 1, the film is cut by a dedicated die/punch device to produce Loders. Diffusion is both via the polymer wall, and also along the fibers (typically when D>50 nm).

The mat is made of coaxial nanofibers (20) that are electrospun and collected on a collector typically in random orientation. The core-shell coaxial electrospinning setup is based on two needles (outer and inner, typically 18 and 22 gauge), pump, high voltage supplier and collector, where the sub-system of the needles can be linearly translated toward the collector. The inner needle is precisely placed coaxially within the outer, and is connected via syringe to a pump, where the outer needle is fed from a surrounding conical feeder.

In this example the shell layer is made of PolyEthylene-Terephthalate (PET). PET is dissolved for example in m-Cresol 5% w/w and the solution is immediately streamed via the outer cone to the outer needle. The amount of PET may optionally be sufficient to form a 5-10% solution; it may optionally be obtained from Sigma Aldrich (Mv ~18,000, IV=0.59 dL/g, d=1.375 g/mL). The core solution comprises siRNA dissolved in aqueous solution 1:10 w/w. The siRNA solution is injected via the inner syringe to the inner needle. The entire setup is set under high electrostatic potential, where the collector is grounded and a high voltage DC is connected to that inner syringe. Fine tuning of the voltage, distance and feed rate is made per specific polymer, solvent, viscosity, conductivity, drug and doses, to obtain a nanofiber having the desired diameter. Without wishing to be limited, optionally the feeding rate typically is 0.1-0.4 mL/h, and is sensitive to viscosity of solutions, voltage is 1-2 kV/cm, and needle distance is 10-33 cm. As a non-limiting example, 0.15 mL/h, 16 kV and 14 cm are selected.

In some embodiments the Loder is built by assembly of tiny polymeric fibers encapsulating the drug. The fibers typically are of micro and nano scale diameter 10 nm-10,000 nm, and are manufactured preferably by electrospinning methods, including methods described in (7-10). In one embodiment the drug is embedded in the polymer and a single fiber is electrospun. In another embodiment the electrospun fiber is hollow (for example coaxial fiber as described in patent application (11)) and drug is embedded during the electrospinning process to the inner fiber by two-needle (two components) electrospinning method (20). In other cases manufacturing methods include Melt spinning (typically for large diameter range 10 um-50 um); and Melt blowing (1-20 um). Other embodiments include polymeric "sponge" and fiber mat.

Example 3

Drugs to be Eluted from the LODER

The drug to be eluted preferably is a gene silencing biological siRNA drug, for example for localized cancer cases in breast, pancreas and prostate as described below. Another indication for example is anti-HIV siRNA. The siRNA can be presented "naked", as the barriers of systemic administrations, and the encapsulation and protecting methods developed to handle them, are either irrelevant here, or protection is provided by the encompassing polymer substrate, such as a matrix for example, of the Loder. The selection still needs to optimize siRNA effectiveness, including uptake. Preferably the siRNA selection is based on considerations including sequence, size, structure, conjugation and chemical modification, as follows (but without desiring to enumerate a closed list; the discussion of conjugation and chemical modification was made previously):

Sequence Determinants:

siRNA preferably features the following four sequence conditions at the same time:

(1) AU richness in the 5'-terminal, 7-bp-long region of the antisense strand;

(2) G/C at the 5' end of the sense strand; and (3) the absence of any long GC stretch of >9 bp in length.

(4) Most potent siRNA has a G/C content ranging from 36% to 52%.

siRNA Size Determinants:

Synthetic RNA duplexes of 25-30 nt in length (more specifically, 27 nt), which are Dicer substrates, have been shown to be up to 100-fold more potent than corresponding conventional 21-nt siRNAs; a two-base 3' overhang directs Dicer cleavage.

siRNA Structure Determinants:

The A-form helix of the guide strand-mRNA duplex is required for the mechanism of RNAi. A 25-30-nt asymmetric dsRNAs with a 5' blunt end and a 2-nt 3' overhang on the other end. A blunt structure at the 3' end is the strongest terminal structure for promoting activation of dsRNA signaling through the PKR pathway, followed by a 5' overhang; this will improve a local anti-cancer effect.

Moreover, many drugs other than siRNA are applicable to be encapsulated in Loder, and can be used associated with this invention, as long as such drugs can be encapsulated with the Loder substrate, such as a matrix for example. Such drugs include approved drugs that are delivered today by methods other than of this invention, including Amphotericin B for fungal infection; antibiotics such as in osteomyelitis; pain killers such as narcotics in a Loder implanted in the vicinity of the spine in the case of back pain.

In different applications such as smooth muscle cells that are injured during a stenting procedure and as a results tend to proliferate, the drug are either siRNA that silence smooth muscle cells, including H19 silencing, or a drug of types including taxol, rapamycin and rapamycin-analogs.

Example 4

Loder Implementation and Usage in Patients with Breast Cancer

The application of a Loder for patients with breast cancer is optimized for breast-conserving surgery or mastectomy may optionally be performed as follows. The therapeutic approaches include but are not limited to: A. Introducing the Loder prior to the surgery as a neoadjuvant treatment. This therapeutic modality is selected to reduce the tumor mass and reduce the metastatic potential upon performing the operation. This approaches is based on recently proven advantages in other tumors in which a pre-surgical medical treatment was administered to reduce the tumor mass and reduce the metastatic potential upon performing the operation. B. Post surgical implantation of the Loder at the tumor bed. This approached is to be undertaken with other therapeutic modalities such as in the case of MammoSite breast brachytherapy. Following lumpectomy a plurality of Loders, typically ≤25, are implanted at the tumor excision borders around the cavity generated at the tumor bed. The number of Loders and precise location is based on the radius of effectiveness of the specific type of Loder, and is preferably between 1 mm to 20 mm. Additional location of implementation is at the regional lymph nodes draining the tumor.

The methods of implantation of the Loders include but are not limited to the following (without wishing to enumerate a closed list):

Direct Implantation of the Loders at the tumor mass and surrounding non-tumor tissue under an imaging method or without as a neo-adjuvant siRNA therapy. Operation could include ultrasound and/or MRI. The Loder is implanted by injection with a directed needle. Alternatively, a Loder, designed with dimensions meeting Gene-Gun constraints, is administered with a "Loder Gun" that is similar to Gene-Gun as is used for vaccination, to implant one or more, typically up to 20 Loders, simultaneously.

Navigating the Loder Through the Mammary Ducts to the direction of the tumor. Implantation into the tumor and non-tumor environment. Under direct vision of ultrasound the Loder is navigated to the tumor site through the ducts to the diseases duct Following the excision of the tumor the Loders are optionally implanted directly in the operation room initially, and if needed also under ultrasound later, to the surrounding tissue in the area of the tumor. This is a type of adjuvant therapy. In this case the Loder is implanted with a needle or a Loder gun as described above. 4. The regional lymph nodes are imaged too and the Loders are implanted directly to these structures. In to the lymph nodes the Loder is directly injected.

The siRNA Targets:

The siRNA targets include all genes on which breast cancer cells are addicted to. Targets include hTERT, Estrogen receptor; progesterone receptor; growth factors, c-Myc, Cyclin D1 and 2, Her2, H19 and other targets (16). The Loder siRNA composition is of a single siRNA type or a mixture of two or more siRNAs. The content/concentration ratio is equal, or in different ratios. Moreover, this invention includes siRNAs (encapsulated in Loder) designed against targets, that will be found in future investigations, proving breast cancer to be addicted to other oncogenes or tumor promoting factors. This statement holds true for the case of Breast cancer as well as for the other cancers or other applications described elsewhere in this invention.

Example 5

Loder Implementation and Usage for Patients with Pancreatic Cancer

Indications of Pancreatic cancer for which the Loder is a suitable treatment include but are not limited to Non-Operable, Neo-Adjuvant, Local Recurrence, Repetitive procedure and Long term analgesia. The Loder treatment for pancreatic carcinoma is used for operable and non-operable patients. A.

Loder for operable patients: One of the major causes of morbidity of pancreatic carcinoma is local invasive tumor growth around blood vessels. Implanting prior to surgery of the Loder as a neoadjuvant local chemo/siRNA therapy has a major advantage (the Loder improves local administration of other chemotherapies e.g. Gemcitabine that was approved by the US FDA in 1998 after a clinical trial reported improvements in quality of life in patients with advanced pancreatic cancer) (14). B. Intraoperative therapy: The Loder is implanted at the tumor bed at the time of operation and also at tumor invasive suspected sites as they are detected during the operation. C. Loder for non-operable patients: A large group of patients with non-operable growth of tumor are treated with the Loder. This treatment is administered directly to the tumor, its local invasive growth or to the metastatic tissue, such as the liver spread. D. In addition, the Loder could be implanted into a metastasis in case there is only few or one such extra-pancreatic tumor.

Typically the procedure steps would include but are not limited to the following:
1. Collection of relevant clinical data e.g. imaging
2. Office visit/Endoscopy suite
3. Gastroscopy/Endoscopy
4. Endoscopic Ultrasound
5. Trans-gastric implantation of the Loder
6. Evaluation of anatomy
7. Next trans-gastric implantation of the Loder (optional)
8. Evaluation of Loder implants
9. Follow-up by clinical, biochemical and imaging means The Method of Implantation of the Loders for Pancreatic Carcinoma:

The Loder is implemented by direct or in-direct approaches, including but not limited to the following (and without wishing to enumerate a closed list):

Direct Implantation is typically under computerized tomography (CT), by which the Loder is inserted with a needle into the tumor tissue. However, this could also be done by other means like ultrasound or MRI). The number of Loders implanted is deduced from the tumor size, and three-dimensional structure as depicted in the imaging system used. Typically, the preferred role is that each Loder will be implanted into ~10 mm diameter volume of tissue, and the interval between each Loder is 10 to 20 mm.

In the operating room following the excision of the tumor mass, the surgeon can implant again with the Loder needle the Loder into the tumor bed walls or into suspected lymph nodes with tumor cells. This is performed with or without an intra-operation ultrasound. The number of Loders is according to the size and shape of the tumor. The Loders are implanted with a needle or a Loder gun.

Administration via an endoscopic retrograde cholangio-pancreatography (ERCP) may optionally be performed as follows The ERCP is approximated to the tumor site and through the biliary or pancreatic ducts a probe is inserted and approximates the tumor and the Loder is injected into the tumor tissue.

Administration may optionally be performed via an endoscopic ultrasound (EU), which enables vision and approximation to the tumor site and the Loders under this vision will be administered into the tumor tissue with a needle or a Loder gun.

Administration using NOTES (Natural Orifice Translumenal Endoscopic Surgery) methods, for example using endoscopic ultrasound (EU), may also optionally be performed.

The siRNA Targets:

The siRNA targets (17) include all genes on which pancreatic cancer cells are addicted to including K-Ras, BRAF, AKT, Myb, Cyclin D, H19, Telomerase and other oncogenic proteins or RNA targets including microRNAs and other non-coding RNAs (18).

Combination Therapy:

The Loder may optionally release one or more additional drugs, in combination with the nucleotide based agent such as an siRNA for example, including but not limited to Gemcitabine and Erlotinib, as well as other examples as given below.

Some non-limiting examples of Loder driven combination therapies are as follows (and without wishing to enumerate a closed list): 1. silencing RNA or alike with chemotherapy such as Gemcitabine. 2. Incorporating two or more siRNAs targeting the same or different messages or non-coding RNAs in the same Loder. 3. Incorporating imaging molecules into the Loder 4. Incorporating immune tolerating or immune stimulating drugs with the silencing RNAs. 5. Combination therapy for the specific target disease; such as siRNA against viral infection in combination with anti viral drugs, one or more. 6. Combining silencing RNA with radioactive substances for local radiation.

Example 6

Loder Implementation and Usage for Patients with Prostate Cancer

The implementation of the Loder may optionally comprise a sole therapeutic modality for prostate cancer; alternatively the Loder is implemented in combination with other treatments. Preferably the Loder features a cylindrical body of 5 mm length and 1.1 mm diameter.

Various non-limiting examples of treatment modalities with the Loder are given herein. 1. For a patient in a watchful waiting program, the patient is typically undergoing biopsy surveillance every 6 to 12 months. These patients are treated with the siRNA or other types (e.g. chemo or hormone ablating drugs) of Loders. Upon performing biopsies or as an unrelated procedure, the Loders are administered. 2. In another example, the Loder is implanted as a neoadjuvant (before surgery) or adjuvant (post-surgery) to a prostatectomy. 3. The Loder may optionally also be implanted with or substituting for the prostate brachytherapy treatment. In case it is given in combination this enables both short term radiation and long-term Loder effects.

The Method of Implantation of the Loders for Prostate Carcinoma.

The Loders are implanted with supporting devices under vision according to a method optionally including but not limited to one of the following (without wishing to enumerate a closed list):

Direct Implantation is performed through the skin of the perineum (the area between the scrotum and anus) using ultrasound guidance or any other imaging device. The Number of the Loders implanted is according to the tumor/prostate tissue. Typically for each 10 mm diameter one Loder is implanted. Implantation is performed with a Loder implantation needle or a Loder gun.

Indirect Implantation is performed with rectal ultrasound. The Ultrasound probe is inserted through the rectum, and a side device used for prostate biopsies is used to navigate the Loder Needle to the tumor/prostate tissue.

In the Operating Room the Loder is implanted in the tumor bed upon direct vision. Also suspected lymph nodes are implanted with the Loder either with a needle or a Loder gun, which is based on existing gene-gun devices.

The siRNA Targets:

The siRNA targets may optionally include one or more of all those genes on which prostate cancer cells are addicted or depend on including HER2/neu, Androgen Rec, AKT, H19, Telomerase (hTERT), hTR and others (14).

Example 7

More Implementation and Usage of Loder

More modalities that are based on implanting Loders include but are not limited to (and without wishing to enumerate a closed list):

Implantation into Tumor Cavities Via Different Scopes.

One treatment is the implantation of the Loder into the Bladder wall in case of bladder carcinoma. This is done with a cystoscopy. In addition, in a similar approach treatments with Loder are based upon using other scopes including endoscope for esophageal cancer, and the laryngoscope for upper airway tumors. Also, Loder is administered into the lung tissue through bronchoscopy.

Per-Cutaneous Implantation.

Another modality is for tumors that are approached directly through the skin, as the head-and-neck cancer. Loder is directly implemented via injection appliance through the skin into the tumor tissue. The Loder dimensions are optimized to the injection device, including currently approved devices.

Intra-Operational.

The implantation of the Loder is performed in the operating room into the tumor bed. Such a case is upon craniotomy for the treatment of Glioblastoma multiforme. The surgeon implants the Loder into the brain tissue surrounding the tumor at the end of the surgery. Implementing the Loder into the brain tissue is done by the same stereotactic approach.

Drug Embedded in Polymer Substrate Associated with Stents, Grafts, Valves and More Devices Implanted within the Vascular System, Including Coronary Arteries, Peripheral Arteries, Veins, Bypass Grafts Such as CABG, and within the Heart.

In such a plurality of cases the drug typically is siRNA that inhibit proliferation of smooth muscle cells (unlike toxic drugs used in current drug eluting stents such Taxol, Rapamycin (Sirolimus) and Rapamycin-analogs). The device in one embodiment is similar to DES such as Taxus (BSC) or Cypher (JandJ), Endeavor (Medtronics) and Xience (Abbott), but with RNAi drug, and the implementation is by the same balloon expendable stenting or self expendable stenting procedures. In other cases the RNAi drugs are encapsulated in a polymeric skeleton or a polymeric substrate, such as a matrix for example, of a polymeric stent, typically made of biodegradable polymer, where the bio-degradation time is not shorter than the effective period of the drug to be eluted. In other case the device is implanted stand alone, where the device is a pure eluter with no stenting functionality, namely there is no function of opening a vessel.

RNAi Drug or Plurality of Drugs are Encapsulated in Polymeric Substrate, Associating with, and in Some Cases Function as Covering of, Non-Vascular Stents.

Non-vascular stents include stents for the gastro-intestinal system, including esophagus, biliary duct and intestine stents, and stents for the bronchus and tracheas. The implementation is similar to stenting operations of such stents including stenting with endoscopy.

Loder Implementation and Usage for Patients with Carcinoma of Esophagus.

Indications include but are not limited to Non-Operable (amongst are Mechanical obstruction of esophagus, Metastasis, Erosion and bleeding, Pain-dilation of esophagus); Neo-Adjuvant for example in the case of Large tumors with local invasion; Local Recurrence (include slowing down the tumor growth, Prolong survival, Pain control); Repetitive procedure and Long term analgesia.

The process may optionally include but is not limited to the following steps:

1. Collection of relevant clinical data
2. Office visit/Endoscopy suite
3. Esophagoscopy and Gastroscopy
4. Mucosal flap (EMR technique)
5. Direct implantation of one or more Loders under the mucosal flap
6. Mucosal closure
7. Endoscopic Ultrasound
8. Evaluation of Loder implants Example 8

Extended, Controlled Release of Model Substances from the Loder

The ability of substances to be released for an extended period of time from the Loder in a controlled manner was tested with two model substances, methylene blue and lysozyme. Methylene blue is much smaller than siRNAs (only about 320 daltons), while lysozyme (14,500 daltons) is a similar molecular weight to siRNAs. Both showed generally similar release profiles from the Loders, with an initial rapid release that quickly plateaued to a slower, extended release over a period of many days (up to 60 days).

Materials and Methods

Figure 2A:
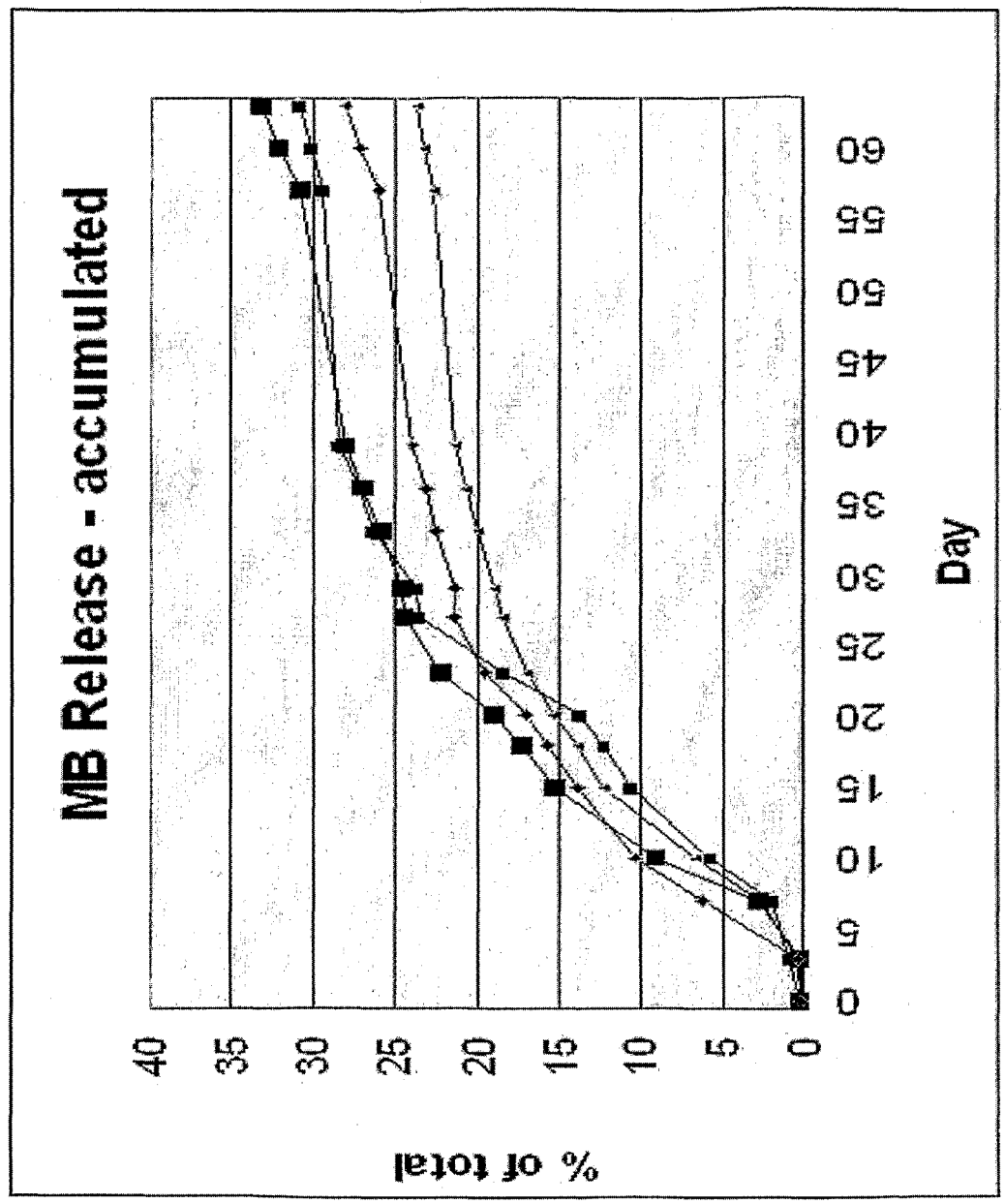
FIG. 2 shows results for release of methylene blue from the Loder, demonstrating 62 day release of stable and fairly constant rate.
Figure 2B:
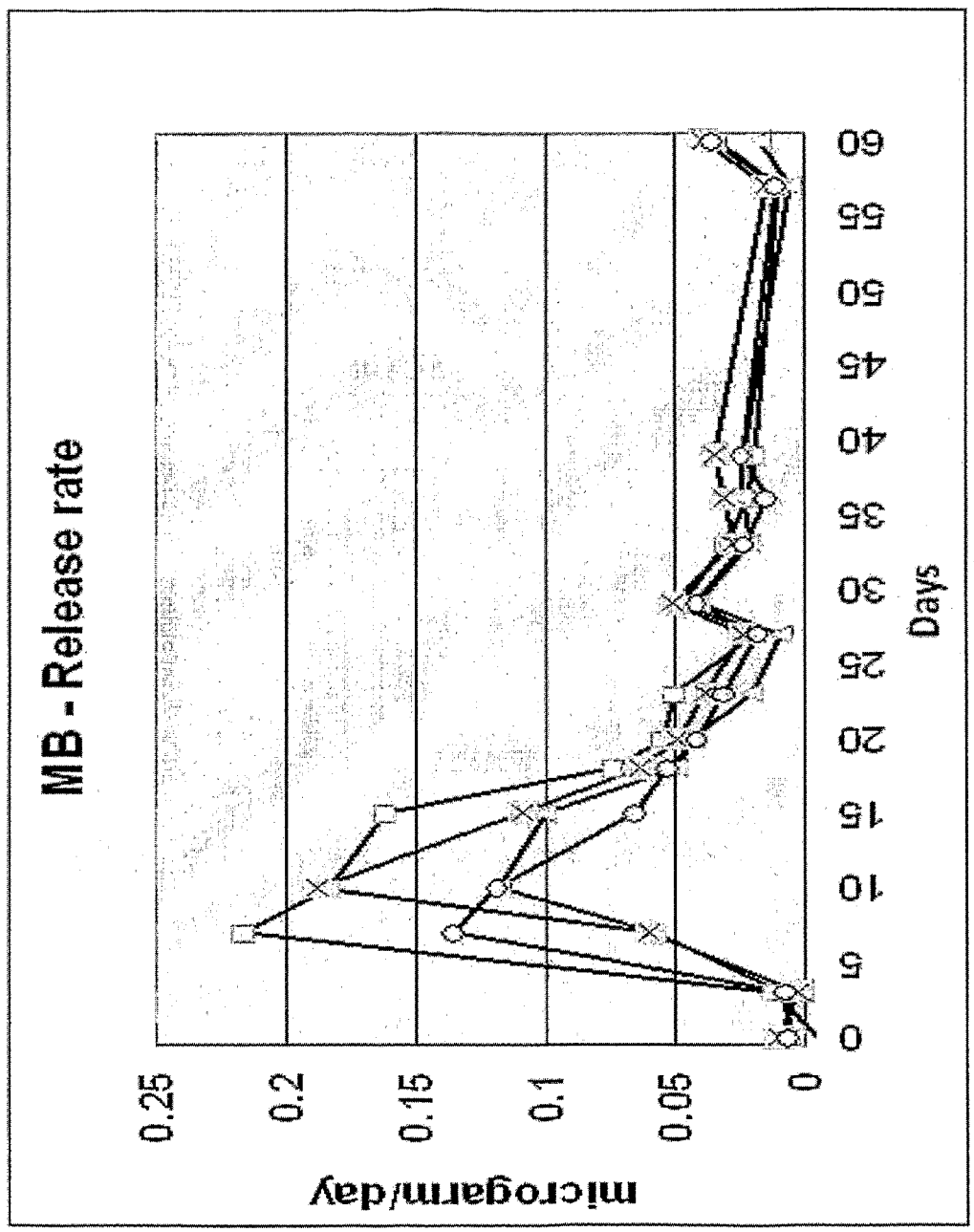
Figure 2C:
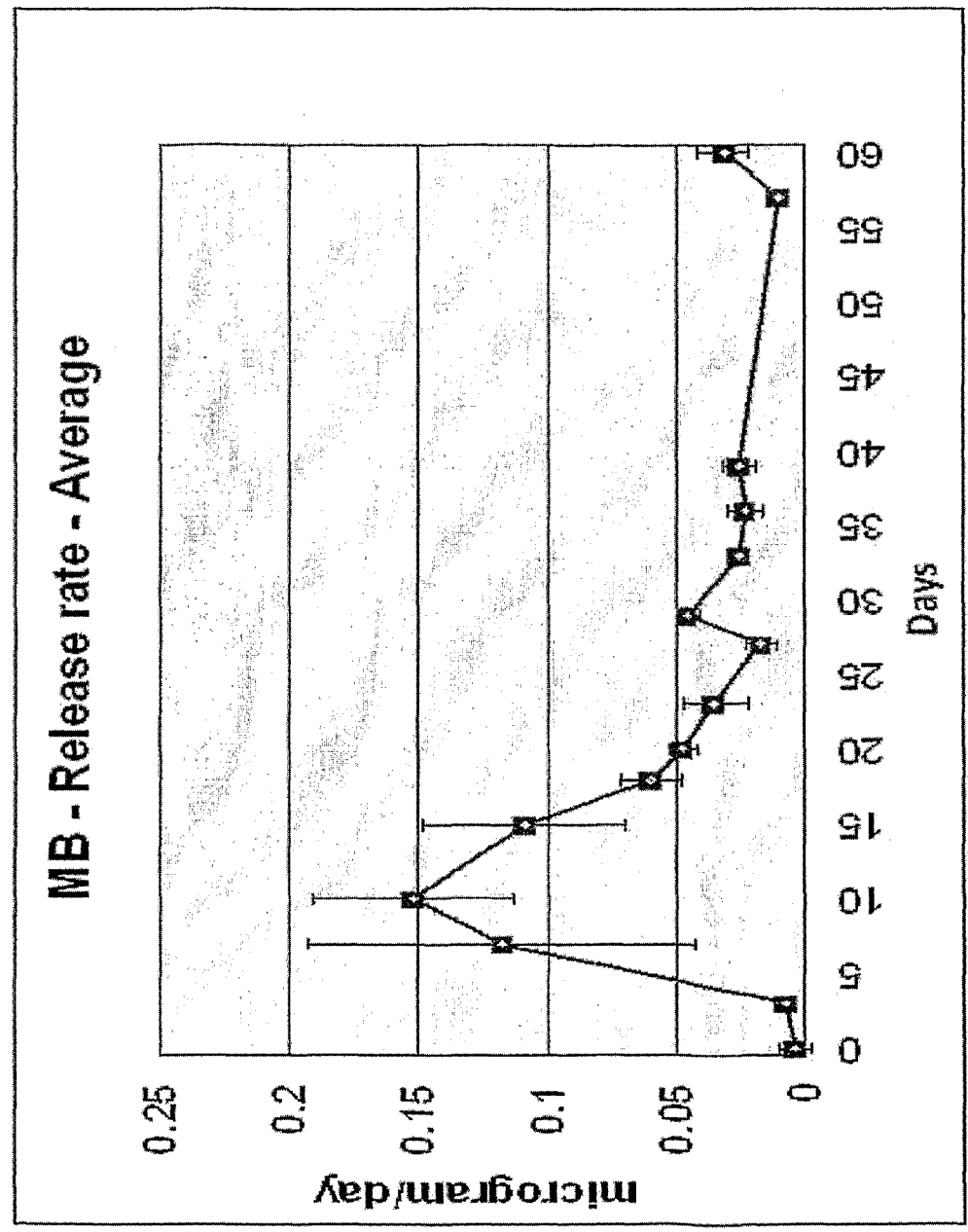
Figure 3A:
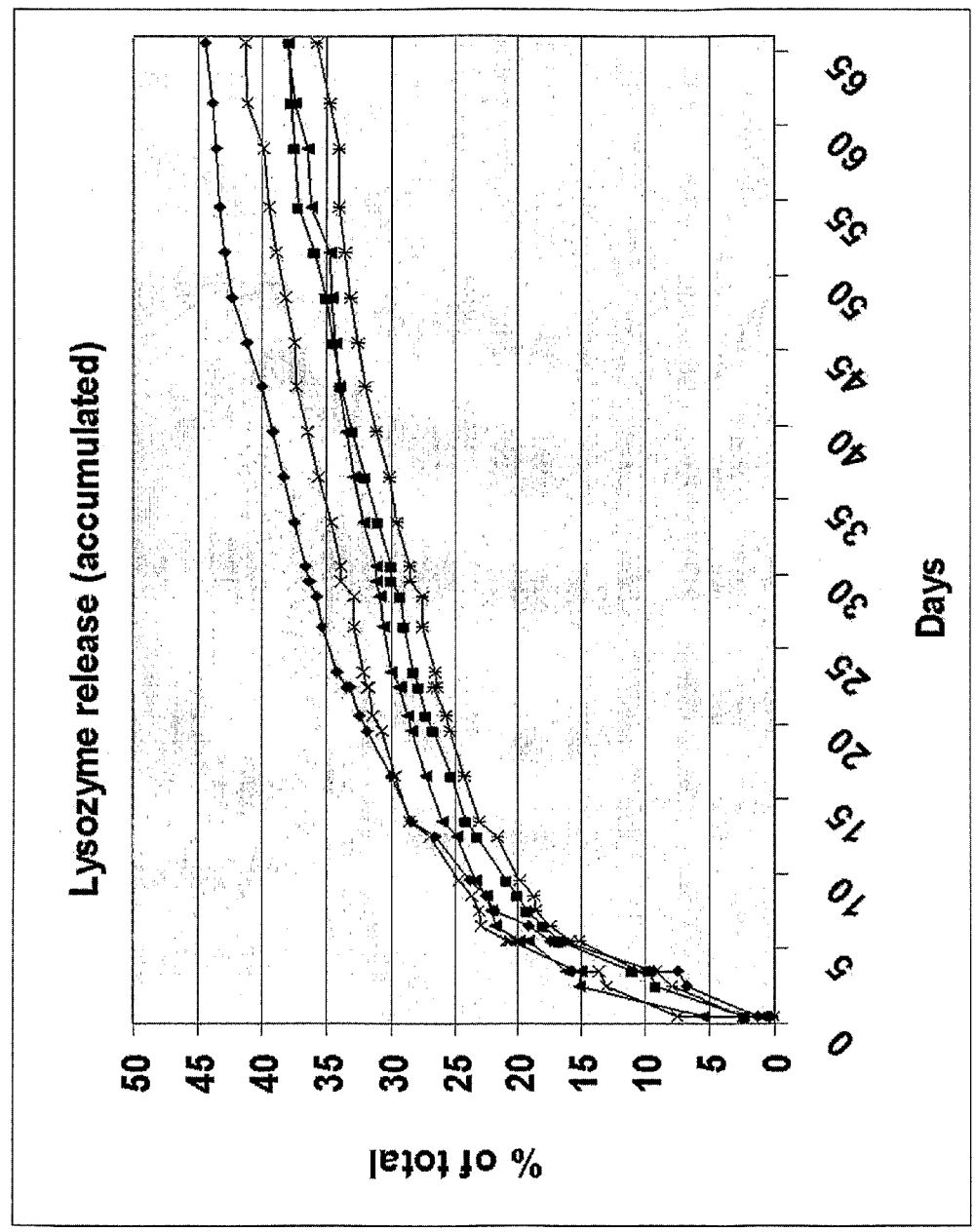
FIG. 3 shows the results for release of lysozyme from the Loder, also demonstrating 65 day release of stable and fairly constant rate, here for a compound whose molecular weight is similar to siRNA.
Figure 3B:
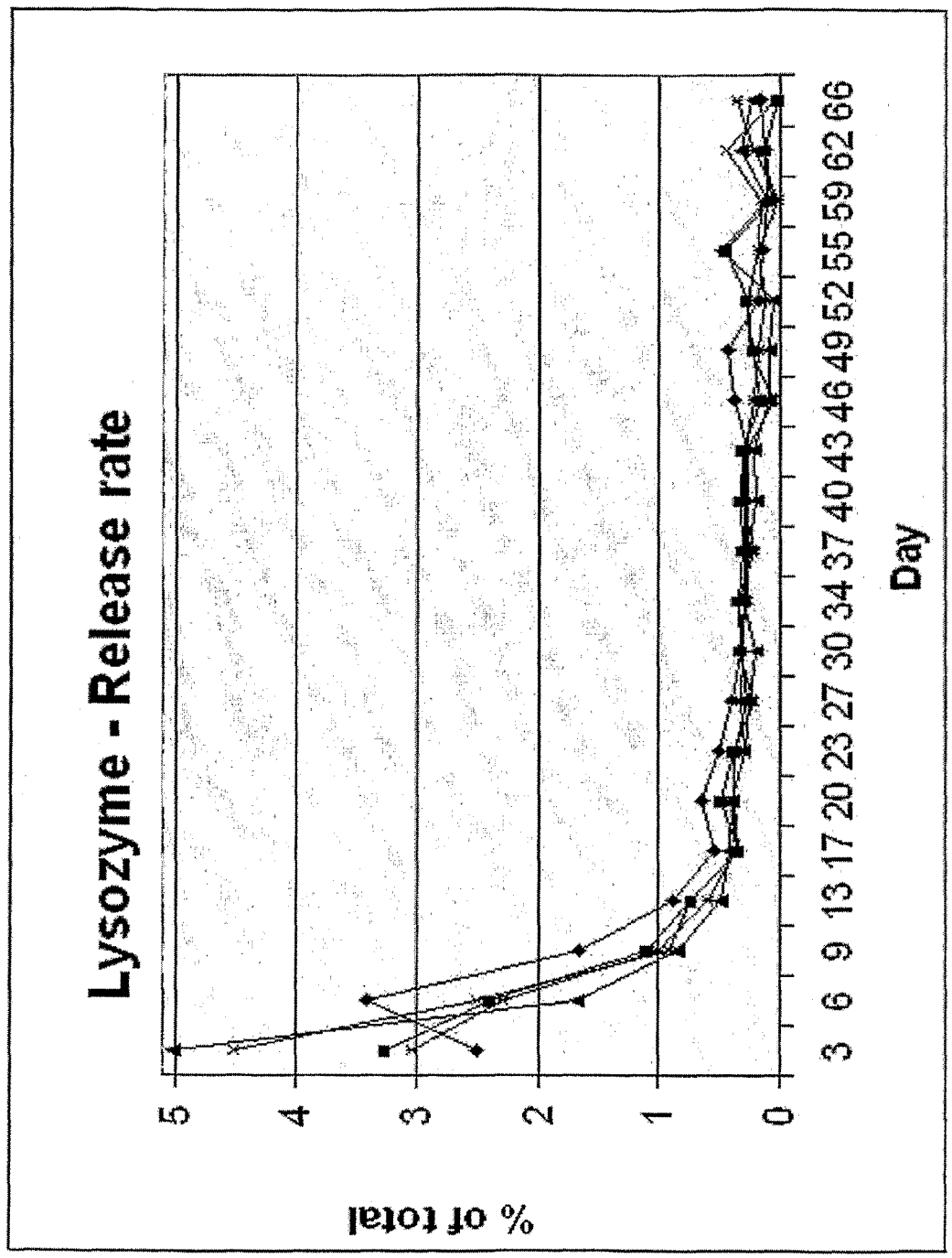
Figure 3C:
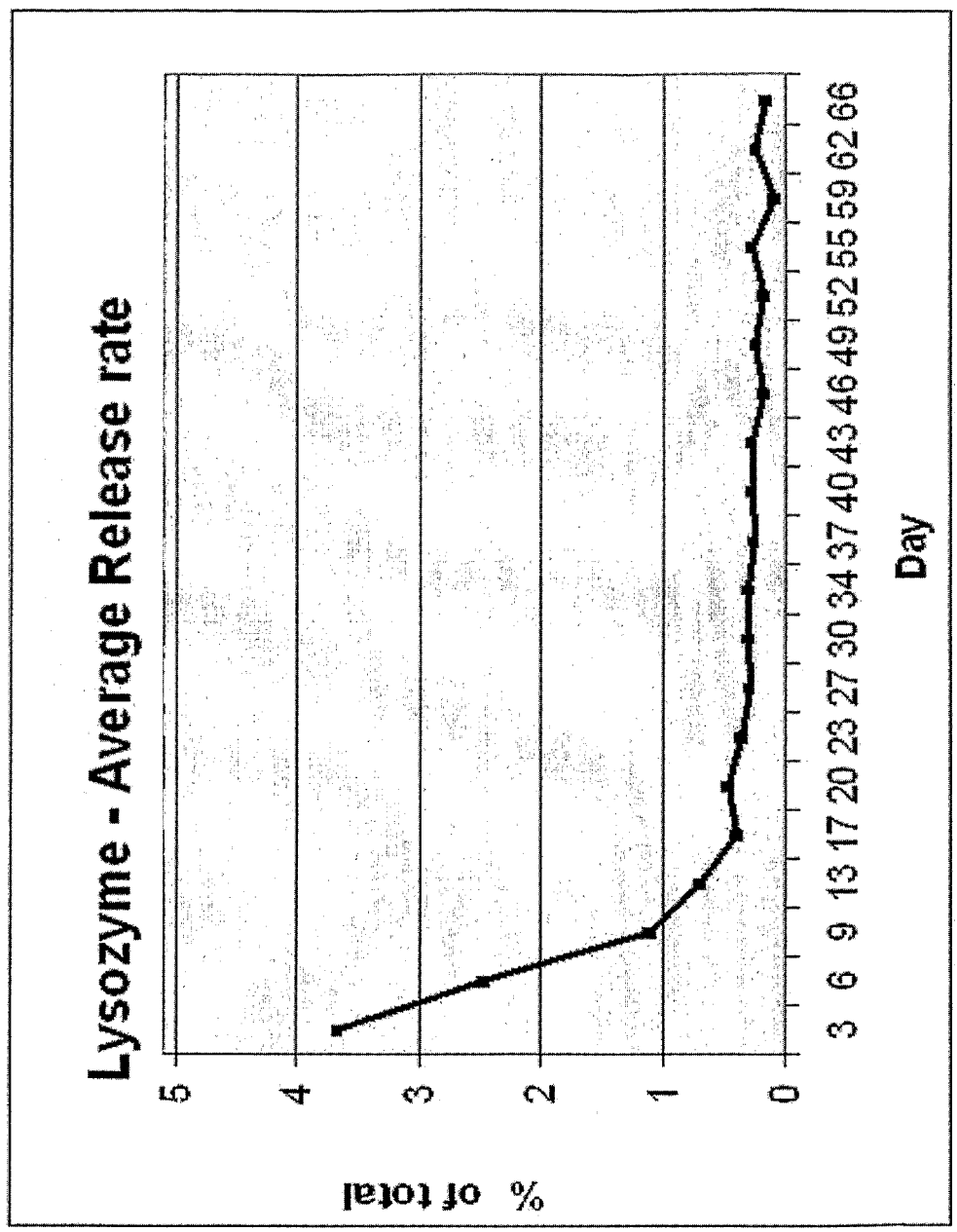

Methylene blue was obtained from J. T. Baker Inc. Lysozyme was obtained from Sigma Aldrich. Loder materials were obtained from (PLGA-Sigma Aldrich or Purac, Mannitol—J. T. Baker Inc.). The Loders were prepared by the process described in Example 1.2. For the methylene blue experiment, each Loder contained 9 micrograms of methylene blue in 1.5 grams PLGA (PLGA (50:50) Mw: 40,000-75,000). The Loder was then incubated in PBS buffer at 37° C. for 60 days. During this time period, samples of 1.5 microliters were periodically removed from the incubation buffer and were tested in a Nanodrop ND-1000 Spectrophotometer according to manufacturer's instructions to determine OD. Results are shown in FIGS. 2A-2C, described in greater detail below. For the lysozyme experiment, each loader contained 0.45 mg lysozyme (45 mg Lysozyme in 450 mg PLGA (PLGA (50:50) Mw: 150,000(purac)). The Loder was then incubated in PBS buffer at 37° C. for 65 days. During this time period, samples of 1.5 microliters were periodically removed from the incubation buffer and were tested in a Nanodrop ND-1000 Spectrophotometer according to manufacturer's instructions to determine OD. Results are shown in FIGS. 3A-3C, described in greater detail below.

Results

Loders loaded with lysozyme or methylene blue both showed extended, controlled release profiles that overall were quite similar, indicating that the characteristics of the Loder itself, rather than the loaded material, determined the released profile.

The results for release of methylene blue from the Loder are shown with regard to FIGS. 2A-2C. FIG. 2A shows cumulative release; the x axis shows the number of days since release was initiated and the y axis shows the total percent of methylene blue released, with one curve per Loder. FIG. 2B shows the release rate in micrograms per day, with the y axis showing the number of micrograms released and the x axis showing the number of days since release was initiated, with one curve per Loder. FIG. 2C shows the average release rate in micrograms per day for all Loders, with the y axis showing the number of micrograms released and the x axis showing the number of days since release was initiated.

As shown in FIG. 2A, the rate of cumulative release over 60 days first rises rapidly until about day 15, after which the rate plateaus. However, methylene blue continued to be released and the cumulative amount released continued to increase even at day 60, indicating that the Loder supported extended release for a period of at least 2 months. FIGS. 2B and 2C both show a peak in the release rate around days 10-15, followed by a rapid drop in the rate of release to reach a plateau around day 25. Although there is some variability between Loders, which may be an effect of the preparation process or of the amount of material actually loaded, the overall trend is clearly shown by the release patterns from all Loders.

Turning now to the experiments in which lysozyme was loaded, the results for release of lysozyme from the Loder are shown with regard to FIGS. 3A-3C. FIG. 3A shows cumulative release; the x axis shows the number of days since release was initiated and the y axis shows the total percent of lysozyme released, with one curve per Loder. FIG. 3B shows the release rate in micrograms per day, with the y axis showing the number of micrograms released and the x axis showing the number of days since release was initiated, with one curve per Loder. FIG. 3C shows the average release rate in micrograms per day for all Loders, with the y axis showing the number of micrograms released and the x axis showing the number of days since release was initiated.

As shown in FIG. 3A, the rate of cumulative release over 65 days is highest at day 3, after which the rate plateaus. However, lysozyme continued to be released and the cumulative amount released continued to increase even at day 65, indicating that the Loder supported extended release for a period of almost one month and possibly longer. FIGS. 2B and 2C both show an initial peak in the release rate around day 3, followed by a rapid drop in the rate of release to reach a plateau around day 15. Although there is some variability between Loders, which may be an effect of the preparation process or of the amount of material actually loaded, the overall trend is clearly shown by the release patterns from all Loders.

Example 9

In Vivo Administration of siRNA Against a Specific Tumor Gene Inhibits the Growth of the Tumor A description of this experiment and its results was previously published (Ma'atuk et al, PLoS ONE. 2007 Sep. 5; 2(9):e845—given below as reference 27). The figure is reproduced for completeness.

Materials and Methods
Described thoroughly in Ma'atuk et al., PLoS ONE. 2007 Sep. 5; 2(9):e845 (ref 27).

Results
To examine the effect of H19 siRNA expression on bladder carcinoma tumor formation in vivo, one million human bladder carcinoma cells (UMUC3) cells were injected subcutaneously to athymic nude mice (n=3 for GFP siRNA, and 5 for H19 siRNA), 48 hours following transient transfection with the noted siRNAs. Palpable tumors were observed 6 weeks later in 2 out of 3 mice of the GFP siRNA group, while in none of the H19 siRNA group. Mice were sacrificed 8 weeks after inoculation.

FIG. 4 shows mean tumor volumes (right panel, P<0.05), and mean tumor weights (left panel, p<0.06). Values represent end-points just before and after sacrificing animals. As can be clearly seen, the H19 siRNA group values are near zero, whereas the GFP siRNA group values are between 0-0.6 for the mean weights and between 0-1 for the mean volumes.

The results show that a specific siRNA may be used for the treatment of a specific cancer.

Example 10 si-GFP-Containing LODER Specifically and Potently Inhibits GFP Expression In Vitro This Example relates to the ability of siRNA released from a Loder according to some embodiments of the present invention to inhibit a cell function, in this case GFP expression, in vitro.

Materials and Methods
The Loder materials were described above. The Loder was constructed according to the following process per example 1: In the example: siRNA=si-GFP; siLUC, from Darmacon, TR=Lipofectamine 2000 (Invitrogen). X=10% PLGA; D=2.1 mm. The drug load per Loder in this example is 4 ug.

CT-26 cells stably expressing the EGFP protein (CT26-GFP) were seeded in 48-well plate: $2.5 \times 10^4$ cells/well in a total of 200 ul RPMI medium, containing 10% fetal calf serum and supplemented with penicillin (180 units/ml) and streptomycin (100 µg/ml). The following day the medium was replaced and the noted Loders were added to the medium. 72 hrs later the cells were harvested and analyzed by FACS.

Results
FIG. 5 shows the expression of GFP in CT26-GFP cells that were incubated for 72 hours with a Loder containing the noted siRNAs. The y axis shows expression of GFP as a mean fluorescent intensity. Average mean GFP intensity of 3 samples is shown with the standard error. The bar graph shows the results for the following conditions:
1. "Untreated"—control, without Loder and/or Transfection Reagent (TR) Lipofectamine 2000
2. "Loder only"—control, Loder containing neither siRNA nor TR
3. "Loder+TR"—control, Loder with TR, without siRNA
4. "Loder+siGFP complexed with TR"—TR was pre-complexed with the si-GFP siRNA before encapsulation into the Loder.
5. "Loder+siLUC complexed with TR"—TR was pre-complexed with the si-LUC (siRNA against luciferase) before encapsulation into the Loder.

As can be seen in FIG. 5, si-GFP (and not si-LUC) released from a Loder significantly inhibited the expression of the GFP reporter gene (case 5).

Example 11 siRNA against KASG12D Specifically Inhibits the Expression of Mutant KRAS In Vitro This Example represents the ability of transfected of Loder-derived siRNA to eliminate a tumor, which requires expression of the protein targeted by the siRNA for viability. The Panc1 pancreatic cell line was used; its growth is known to be dependent on the expression of a mutant KRAS protein, KRASG12D. The results show that inhibition of KRASG12D expression in Panc1 cells by either transfected or a Loder-delivered siRNA (si-KRASG12D) leads to cell death.

Materials and Methods
Semi-Quantitative PCR
Pancreatic carcinoma Panc1 cells (expressing a mutant KRAS protein, KRASG12D) were seeded in 6-well plate in DMEM medium containing 10% fetal calf serum, and supplemented with penicillin (180 units/ml) and streptomycin (100 µg/ml), to 70% confluence. The following day, cells were transfected with 1 nmoles of si-GFP (unrelated siRNA) or si-KRASG12D siRNAs for 48 hours using a transfection reagent Lipofectamine 2000, according to the manufacturer's protocol. Forty eight hours following transfection, the cells were harvested, RNA was extracted and cDNA was prepared using the Moloney murine leukemia virus reverse transcriptase (Promega) with random hexamer primers (Promega). The resultant cDNA was then subjected to PCR using the following primer sets: KRASG12D sense 5' CTTGTGGTAGTTGGAGCTGA 3'; antisense 5' CTGTTCTAGAAGGCAAATCAC 3'; GAPDH sense 5' ACCACAGTCCATGCCATCAC 3'; antisense 5' TCCACCACCCTGTTGCTGTA 3'. Band intensity was determined using the TINATM software and normalized to that of GAPDH.

Cell Viability Assay

Panc1 cells were grown as noted previously. To assess cell viability, $0.5 \times 10^4$ cells/well were seeded in 96-well plate. The following day, medium was changed and the cells were mock-transfected or transfected with si-KRAS or si-KRASG12D (25 pmoles, or as noted), using Lipofectamine 2000 transfection reagent (1 µl), according to the manufacturer's procedure. Cell viability was assessed using the Cell proliferation Kit (XTT assay) (Biological industries, Beit Haemek, Israel), according to manufacturer's protocol. Cell death was assessed using Cytotoxicity Detection Kit (LDH assay) (Roche), according to manufacturer's instructions.

Loder Preparation

The Loder was prepared as described in Example 1.1.

Treatment of Cells with Loder

Loders containing the noted siRNAs were added to fresh culture medium, in addition of the noted amounts of Lipofectamine 2000 transfection reagent (Invitrogen) and were incubated with the cells.

Luciferase Expression Assessment

Luciferase expression was assessed using the Dual-Luciferase Assay System (Promega), according to the manufacturer's instructions.

Western Blotting 48 and 72 hrs following transfection of cells that were plated in a 48-well plate, the cells were homogenized in lysis buffer A (0.25M sucrose; 20 mM Tris pH 7.6, 1.5 mM MgCl2, 10% glycerol, 1 mM EDTA and "Complete mini" protein inhibitor cocktail obtained from Roche Diagnostics, Cat No. 11836153001), incubated on ice for 30 min, and centrifuged at 5000 rpm for 10 min at 40 C and the supernatant was saved. Samples were loaded onto a 10% SDS-PAGE and subjected to western blot analysis. Primary Ab used: anti-KRAS (Santa Cruz Biotechnology, Cat#sc-30), anti-β-actin (MPI, Cat#691001). As a secondary Ab, Dako EnVision System labeled Polymer-HRP anti mouse (cat#K4001) or anti rabbit (cat#K4003) were used. Proteins were visualized by the EZ-ECL chemiluminescence detection kit for HRP (Biological Industries, Israel). Band intensity was calculated using the TINATM software, and then normalized to that of β-actin protein.

Statistical Analyses

Results are presented as mean+/−standard error of the mean. Differences between means were analyzed using the unpaired Student's t-test (one-tailed). A probability value of less than 0.05 was considered statistically significant.

Results

To show specific inhibition of the KRASG12D mRNA by a dedicated siRNA (si-KRASG12D), pancreatic carcinoma Panc1 cells were transfected with si-GFP or si-KRASG12D. 48 hrs later, the level of KRASG12D mRNA was assessed using the semi-quantitative PCR method (FIG. 6). As can be seen, si-KRASG12D significantly reduced the KRASG12D mRNA level by 70% in comparison to the mRNA level following transfection with si-GFP. *$p<0.05$ according In a separate experiment, the antiproliferative effect of si-KRASG12D on Panc1 cells was determined. To assess cell viability in the presence of si-KRASG12D, Panc1 cells were mock transfected with Lipofectamine only or transfected with siRNAs against KRAS (wt) or KRASG12D. 72 hrs later, cell viability was assessed using a XTT assay, which measures the metabolic rate of the cells in the culture. As shown in FIG. 7, there is a ~50% reduction in cell viability in the presence of si-KRASG12D compared to mock-transfected cells. siKRAS transfection results in a less prominent reduction in cell viability.

FIG. 8 demonstrates a dose response effect of si-KRASG12D on Panc1 cell viability (using increasing siRNA concentrations). The experiment was performed as for the results shown in FIG. 7, with the noted siRNA concentrations. It can be seen that si-KRASG12D has a specific and significant (when compared to si-GFP), dose related anti proliferative effect on Panc1 cells. **—$p<0.01$ when compared to si-GFP at the corresponding concentration.

To demonstrate siRNA release from Loders, siRNA released into cell culture medium was quantified using a Nanodrop (ND-1000 Spectrophotometer). FIG. 9 shows cumulative release (in percentage) of siRNA type si-KRas$^{mt}$ (13,000 Da; KRas mutated siRNA), as released from 6 different LODERs containing 0.02 mg si-KRas$^{mt}$ each prepared per Example 1 during one week. LODERs were incubated in PBS buffer at 37 C.°. si-KRas$^{mt}$ release was calculated by measuring OD, using Nanodrop.

Figure 10A:
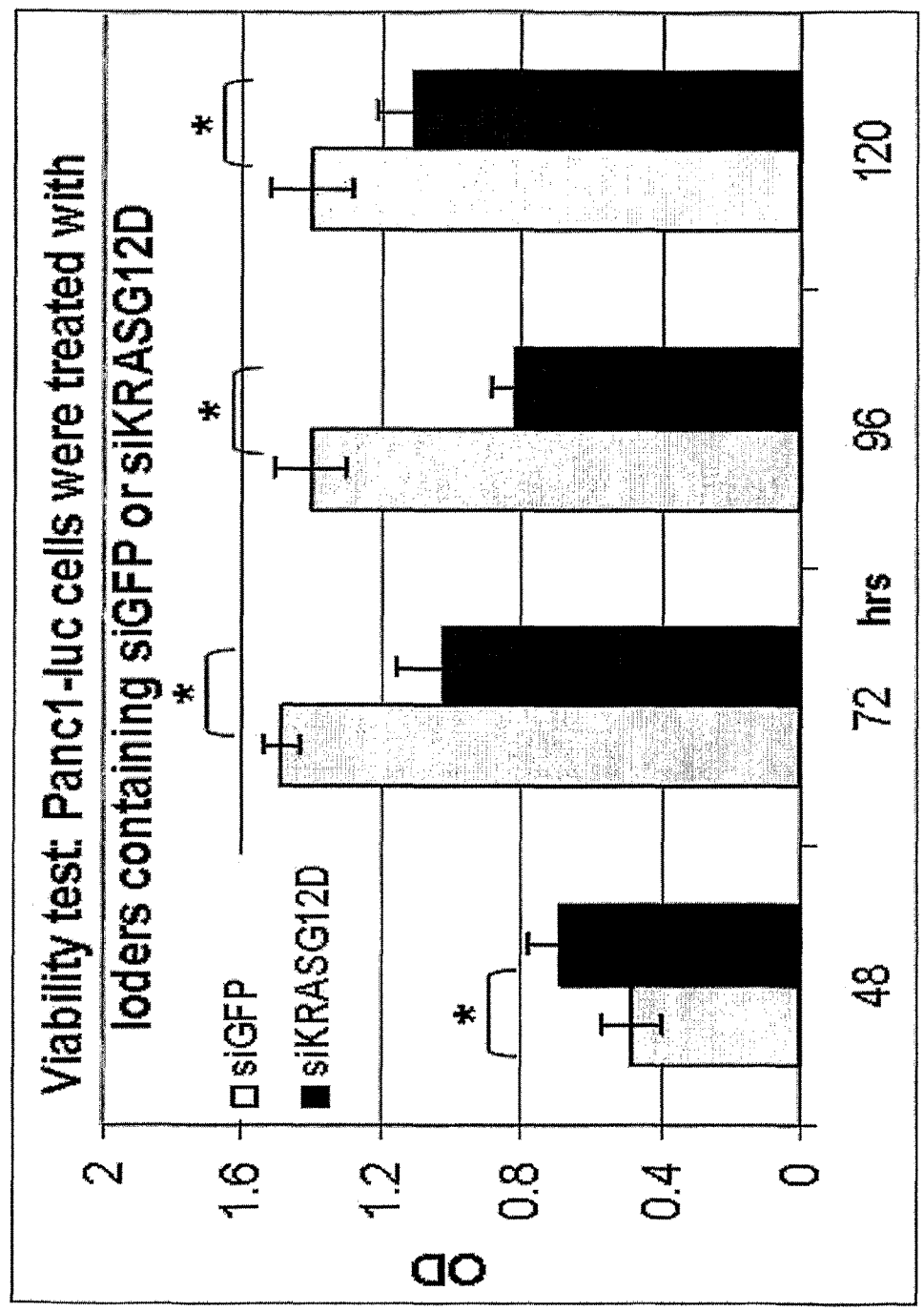
Figure 10B:
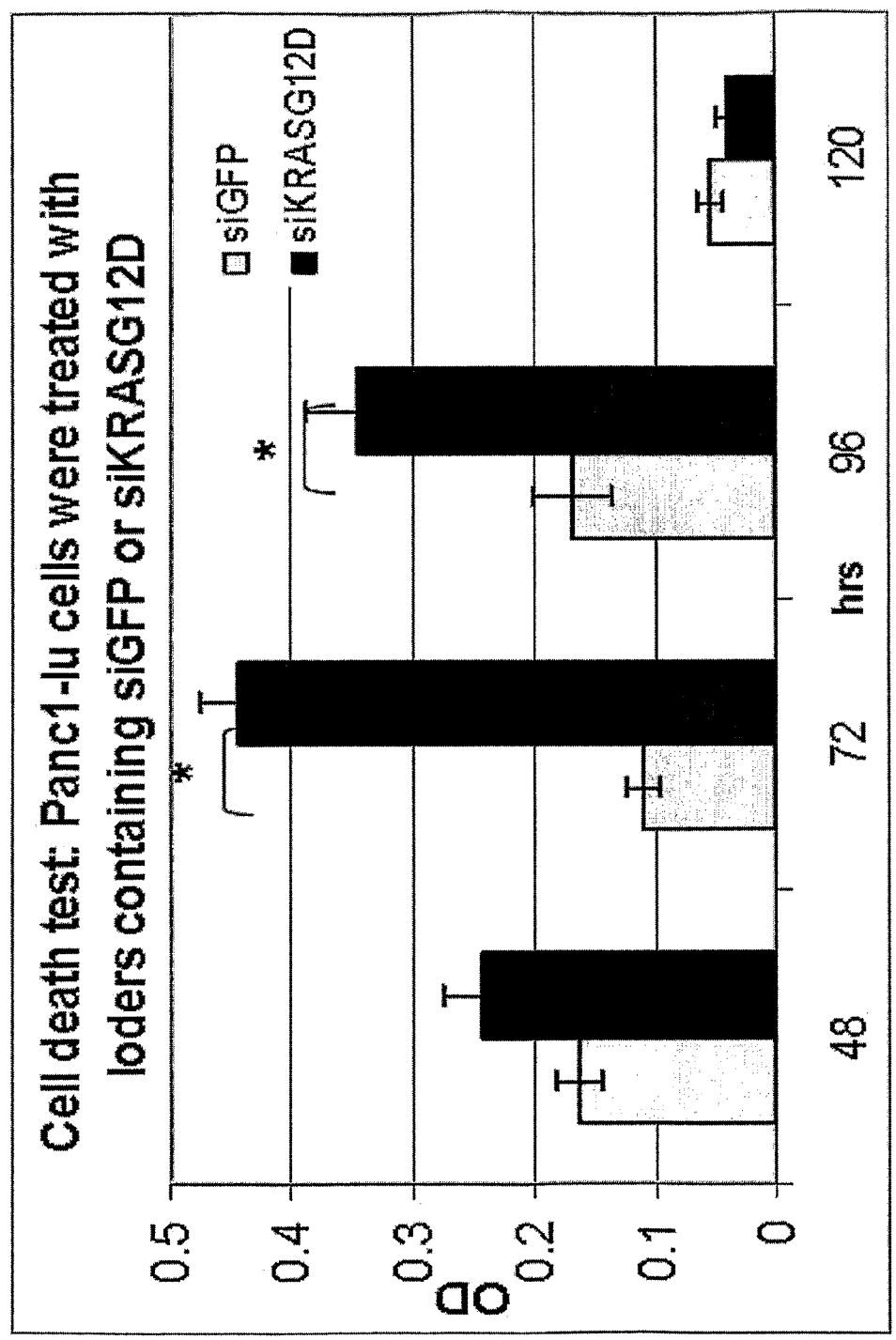

FIG. 10 shows the effect of siRNAs released from Loders on the viability of the pancreatic carcinoma cell line Panc1. Briefly, Panc1 cells stably expressing the luciferase reporter gene (Panc1-LUC) were seeded in 96-well plate as described previously. The following day the medium was changed and Loders containing si-GFP or si-KRASG12D were added to the medium in addition of 1 µl of the transfection reagent Lipofectamine 2000. Cell viability was assessed using the XTT test (FIG. 10A), and cell death was assessed using the LDH test (FIG. 10B). The x axis shows the time in hours after Loder addition, and the y axis shows the measured OD values. The assays were carried out in sextuplets. *—$p<0.05$.

As can be seen, Loder-delivered si-KRASG12D inhibits Panc1 cell viability and leads to cell death.

FIG. 11 shows the effect of releasing siRNAs from the Loders on a pancreatic cell line in comparison to transfection with the siRNAs. Briefly, Panc1 cells stably expressing luciferase gene (Panc1-LUC, clone 15) were incubated with the noted Loders and 2 µl/well Lipofectamine 2000 (FIG. 11A) or transfected with 50 pmoles of the noted siRNAs complexed with 2 µl Lipofectamine-2000 (FIG. 11B). At the noted times, the cells were lysed by a standard procedure and the luciferase expression level was measured using a dedicated kit and a luminometer. The assays were carried out in quadriplicates. The x axis shows the time in hours following treatment with a Loder or control (FIG. 11A), or following transfection with various siRNAs or controls (FIG. 11B). The y axis shows the measured OD values, in this case determined through measuring luciferase levels. Statistical significance was calculated using the t test. **—$p<0.01$ when compared to si-GFP of the corresponding time point.

As can be seen, si-LUC (siRNA against luciferase) released from the Loder reduces the Panc1-LUC luciferase expression level in vitro (FIG. 11A) in a manner comparable to transfection with this siRNA (FIG. 11B). Thus, treatment with a Loder containing the siRNA compares very favorably to direct transfection with the siRNA. The experiment also shows indirectly that Loder-embedded si-KRASG12D inhibits cell viability (there is a reduction in the luciferase level due to a specific cell death mediated by a Loder-derived si-KRASG12D).

FIG. 12 shows Western blot results of an experiment performed as described for FIG. 11, showing the effect of siRNA transfection as opposed to siRNA release from a Loder in vitro on the protein level of the siRNA target in Panc-1 cells. Briefly, Panc1-LUC cells (clone 15) were transfected with 50 pmoles of si-GFP or si-KRASG12D complexed with 2 µl of Lipofectamine-2000, or incubated with Loders containing these siRNAs in addition of 2 µl/well Lipofectamine 2000. 48 hrs (FIG. 12A, B) or 72 hrs (FIG. 12C) later, the cells were lysed and analysed by Western blot. The experiment was performed in quadruples. u/t—untreated cells; **—$p<0.01$ when compared to si-GFP of the corresponding time point.

Figure 12A:
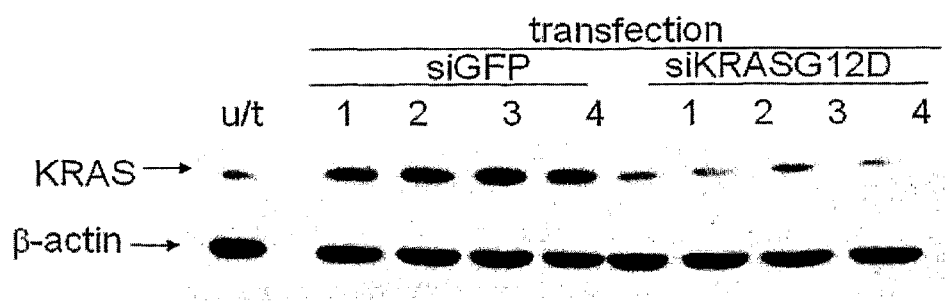
Figure 12B:
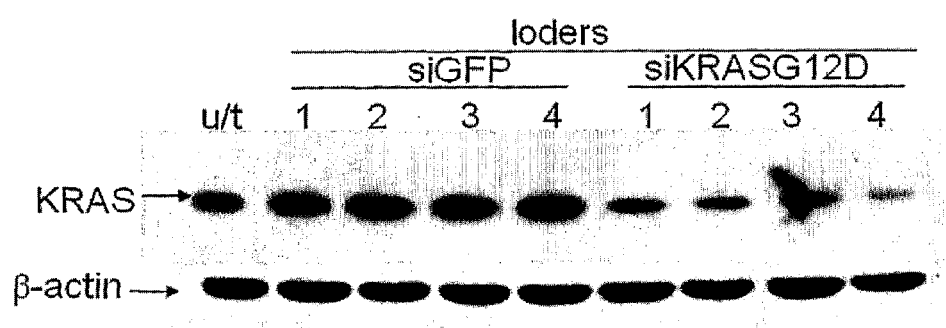
Figure 12C:
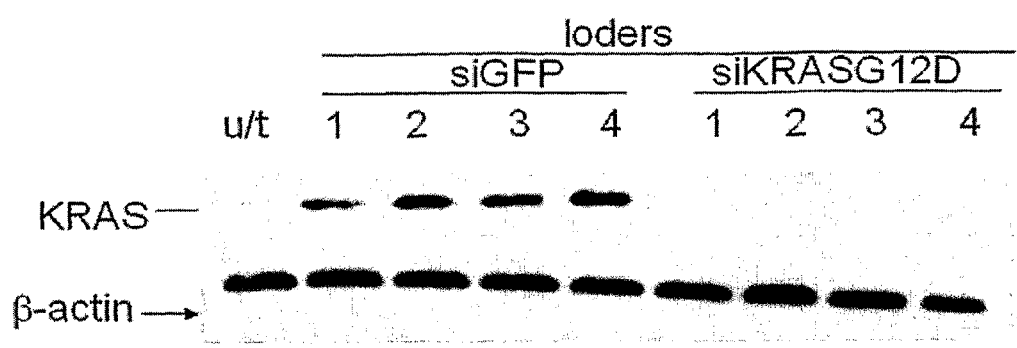
Figure 12D:
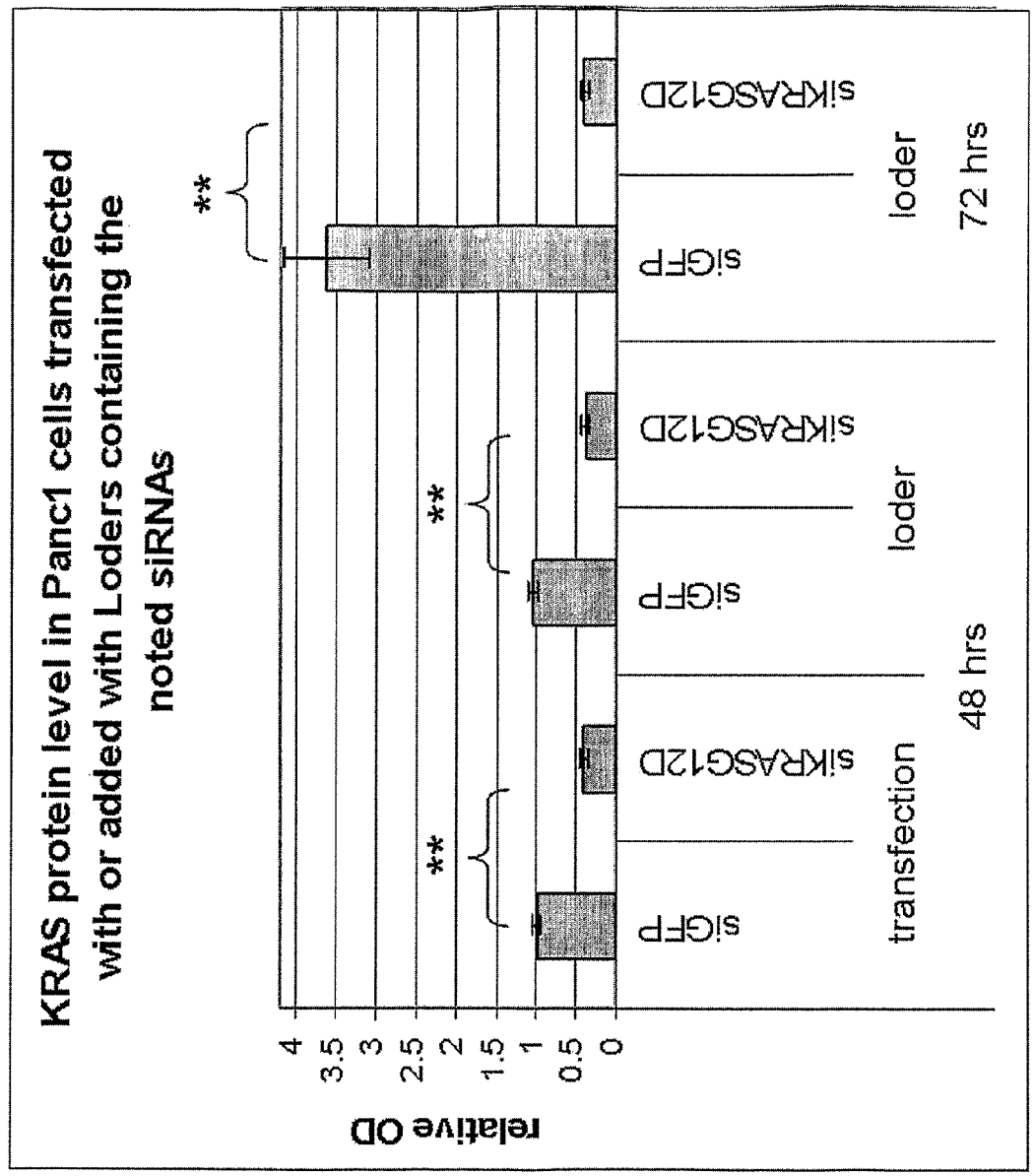

FIGS. 12A and B show total KRAS protein level at 48 hrs following transfection or Loder addition, FIG. 12C shows the results at 72 hrs following Loder addition, and quantification of the bands' intensity (relative to β-actin) is shown in FIG. 12D.

FIG. 12 demonstrates that si-KRASG12D inhibits KRAS protein expression in Panc1-LUC cells, regardless of whether the siRNA was administered through a Loder or by direct transfection. Furthermore, the inhibition of the KRAS protein level caused by Loder-secreted si-KRASG12D is similar to the level of inhibition obtained by transfected si-KRASG12D.

Example 12

Loder-Released siRNA against Luciferase Specifically Inhibits the Expression of Luciferase In Vivo This Example relates to the ability of Loders to release siRNA in vivo, in mice, to cause a functional effect in the tissue of the mice due to the effect of the released siRNA. As described in greater detail below, siRNA released from Loders in mice were able to functionally affect the tissue of a tumor implanted in the mice.

Materials and Methods

10 BALBC mice were injected with 1*10^6 CT-26 cancer cells per mouse that stably express the luciferase reporter gene (CT-26-LUC). Initial luciferase expression imaging using a CCCD camera was performed as previously described (Honigman et al., 2001, Molecular Therapy 4:239-249) 6 days later, to estimate tumor growth in the mice.

The mice were then split into two treatment groups with a similar average luciferase light intensity as calculated by the imaging.

10 days after cell injection, mice of the first group (#1-5) were implanted intratumorally with two siGFP-containing Loders (control, mouse #4 was implanted 7 days post injection), and mice of the second group (#6-10) were implanted with two siLUC-containing Loders (treatment, to show inhibition of luciferase expression due to administration of siRNA). Re-imaging was performed 3 and 7 days after implantation.

Figure 13A:
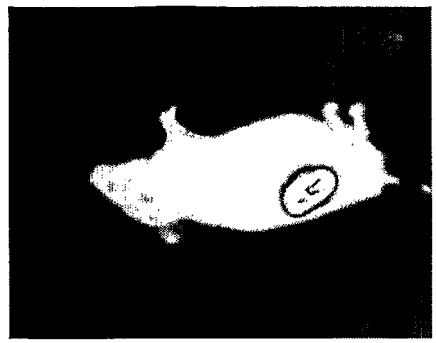
Figure 13B:
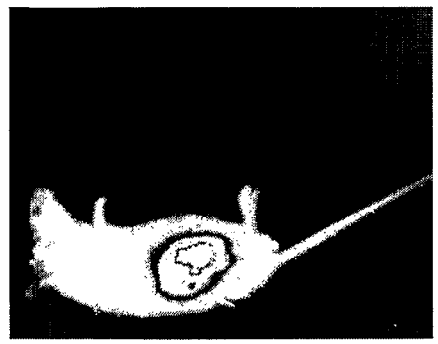
Figure 13C:
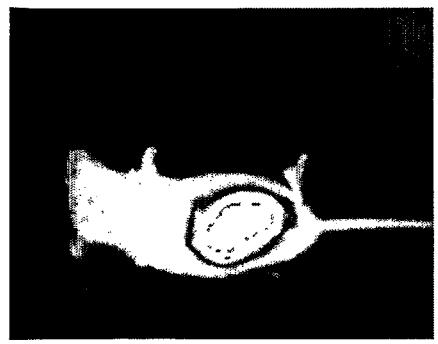
Figure 14A:
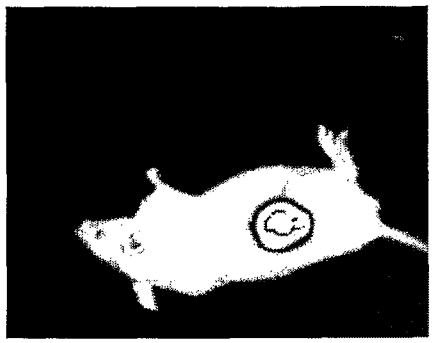
Figure 14B:
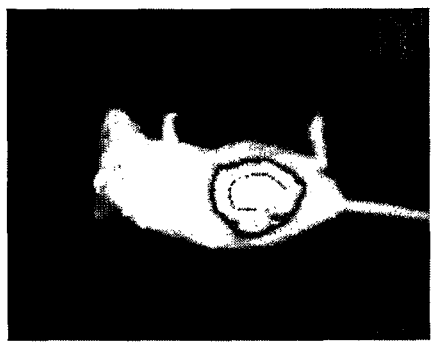
Figure 14C:
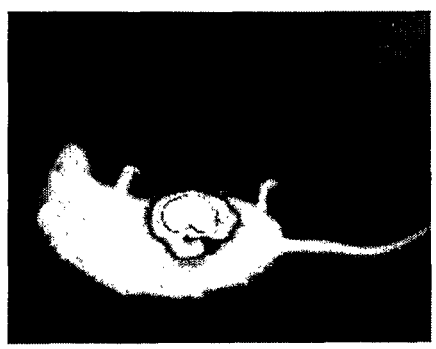
Figure 15A:
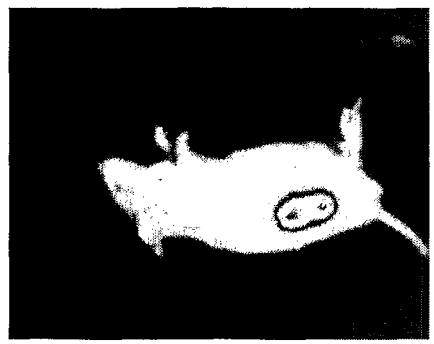
Figure 15B:
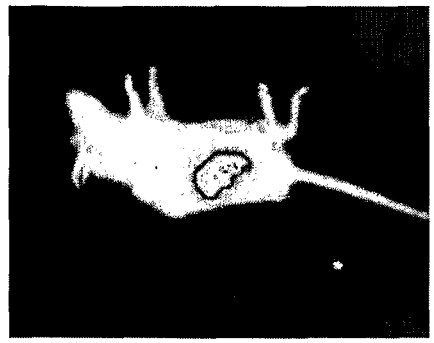
Figure 16A:
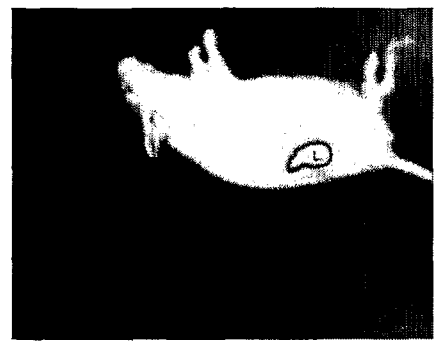
Figure 16B:
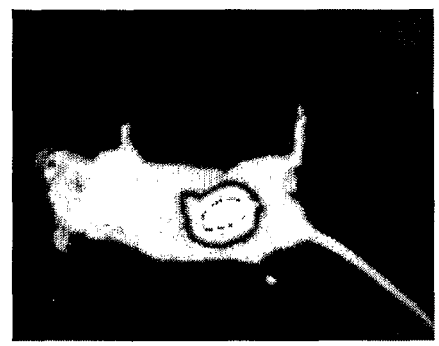
Figure 16C:
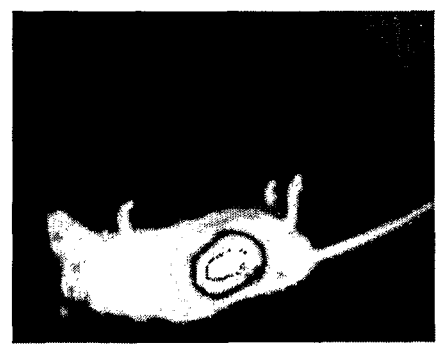
Figure 17A:
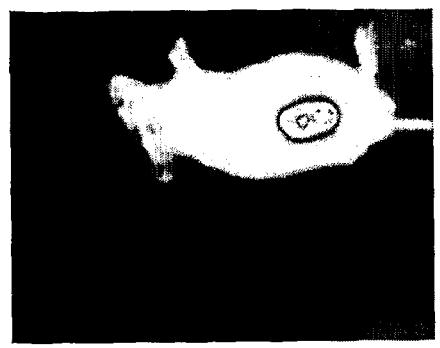
Figure 17B:
Figure 17C:
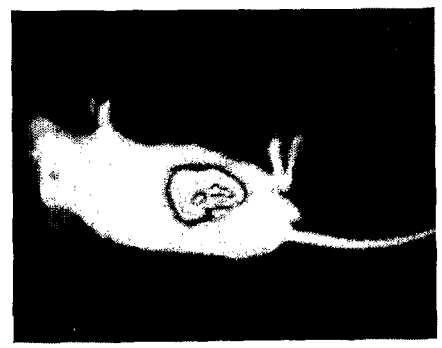
Figure 18A:
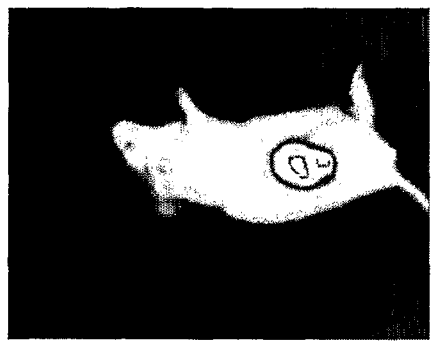
Figure 18B:
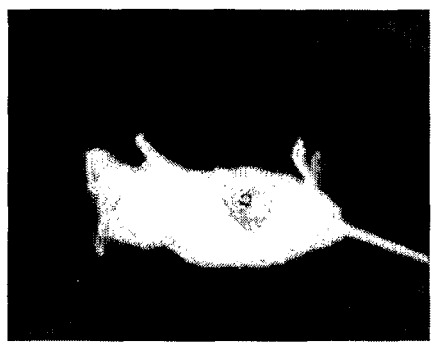
Figure 18C:
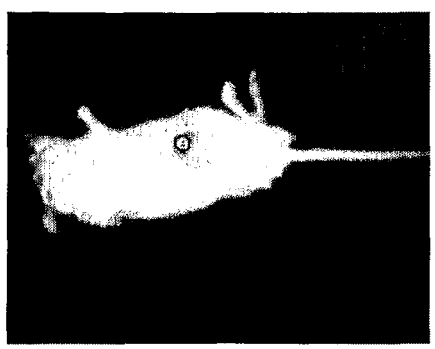
Figure 19A:
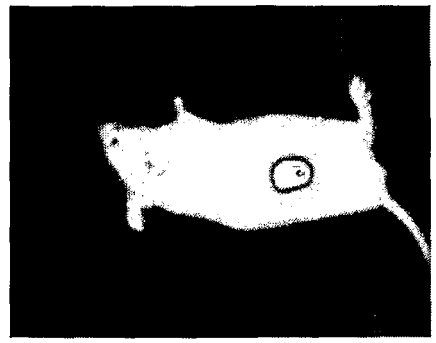
Figure 19B:
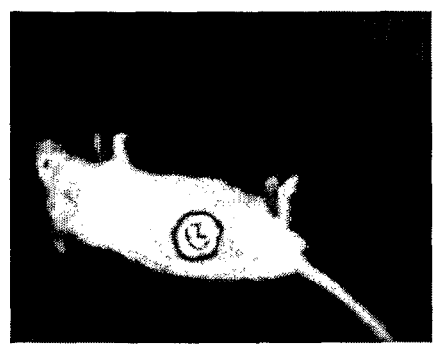
Figure 19C:
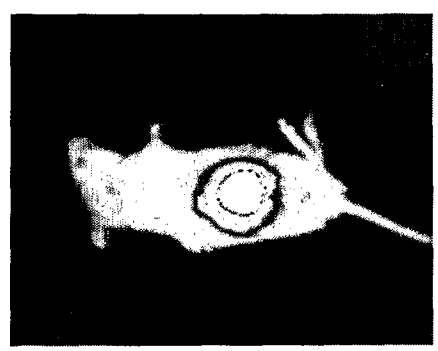
Figure 20A:
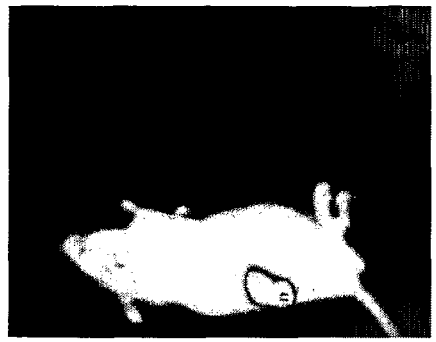
Figure 20B:
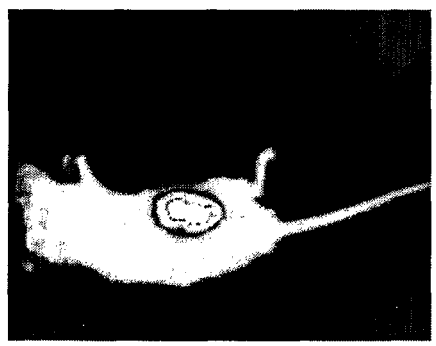
Figure 20C:
Figure 21A:
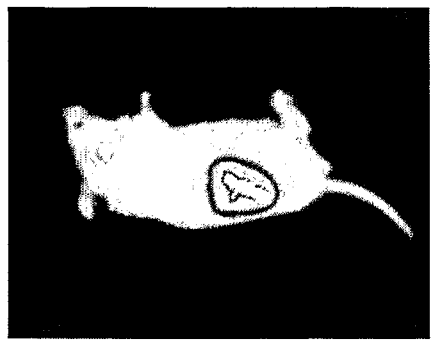
Figure 21B:
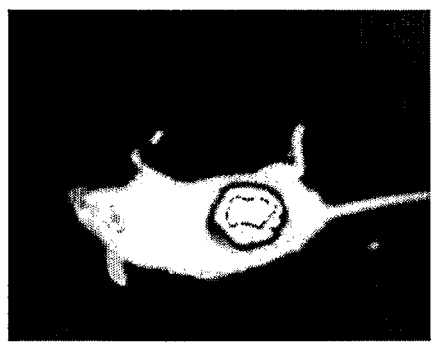
Figure 21C:
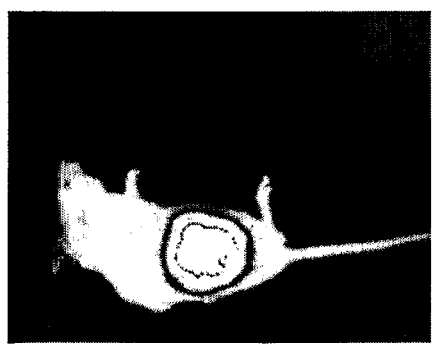
Figure 22A:
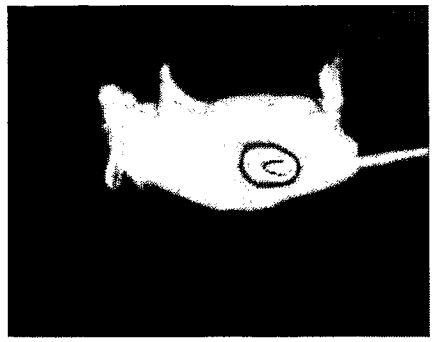
Figure 22B:
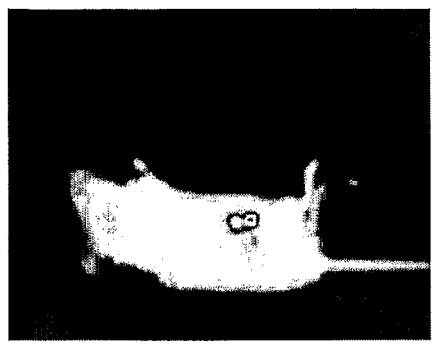
Figure 22C:
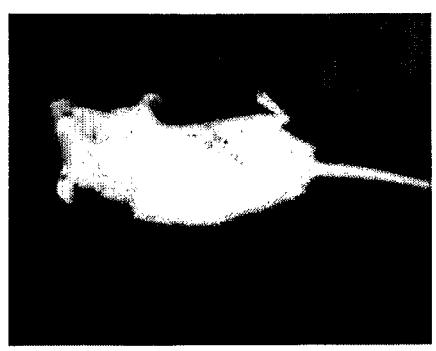

FIG. 13 shows representative pictures of mice transplanted with Loder-si-GFP (left panels) of Loder-si-LUC (right panels) 4 days before (upper panels) or 3 days following Loder transplantation (lower panels). Table 2 summarizes descriptively and FIG. 14 summarizes graphically (average luciferase expression in each mice group with the standard error indicated) the experiment results. *—$p<0.05$ when compared to Loder-si-GFP group.

TABLE 2

A summary of the imaging results of Loder-transplanted mice

| Mouse # | Related Figure | Days post Loder transplantation | Result | Final tumor weight |
|---|---|---|---|---|
| 1 | 13A | −4 | | |
|   | 13B | 3 | Increase in tumor luminescence | |
|   | 13C | 7 | Increase in tumor luminescence | 1068 mg |
| 2 | 14A | −4 | | |
|   | 14B | 3 | Increase in tumor luminescence | |
|   | 14C | 7 | Increase in tumor luminescence | 1653 mg |
| 3 | 15A | −4 | | |
|   | 15B | 3 | Mouse died before last endpoint | NA |
| 4 | 16A | −1 | | |
|   | 16B | 3 | Increase in tumor luminescence | |
|   | 16C | 7 | Increase in tumor luminescence | 506 mg |
| 5 | 17A | −4 | | |
|   | 17B | 3 | Increase in tumor luminescence | |
|   | 17C | 7 | Same or reduced luminescence | 182 mg |
| 6 | 18A | −4 | | |
|   | 18B | 3 | Complete or near complete luminescence inhibition | |
|   | 18C | 7 | Complete or near complete luminescence inhibition | 114 mg |
| 7 | 19A | −4 | | |
|   | 19B | 3 | Significantly reduced luminescence | |
|   | 19C | 7 | Reduced luminescence | 1227 mg |
| 8 | 20A | −4 | | |
|   | 20B | 3 | Reduced luminescence | |
|   | 20C | 7 | Reduced luminescence | 912 mg |
| 9 | 21A | −4 | | |
|   | 21B | 3 | Reduced luminescence | |
|   | 21C | 7 | Reduced luminescence | 1327 mg |
| 10 | 22A | −4 | | |
|   | 22B | 3 | Complete or near complete luminescence inhibition | |
|   | 22C | 7 | Complete or near complete luminescence inhibition | 114 mg |

FIG. 23 shows the average intensity of all mice in each group, GFP (mice 1-5) or LUC (mice 6-10), for each day. siLUC has the most significant effect against luminosity around day 3, by preventing a significant increase in luminosity (even though tumor growth itself was not affected).

FIG. 24 shows a graph of the actual luminosity data (y-axis) as opposed to the number of days after initiation of treatment (x-axis), for mice in each group. There is some variability between mice but the overall trend is clear; siLUC had a significant effect in inhibiting luminosity as opposed to siGFP, when delivered in vivo to the site of a tumor by a Loder according to the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Giladi H, Ketzinel-Gilad M, Rivkin L, Felig Y, Nussbaum O, Galun E. Small interfering RNA inhibits hepatitis B virus replication in mice. Mol Ther 2003; 8:769-776.
2. Galun E. The use of RNAi in gene therapy. World Scientific Publishing 2005:407-437.
3. Ketzinel-Gilad M, Shaul Y, Galun E. RNA interference for antiviral therapy. J Gene Med 2006; 8:933-950.
4. Matouk I J, DeGroot N, Mezan S, Ayesh S, Abu-lail R, Hochberg A, Galun E. The H19 non-coding RNA is essential for human tumor growth. PLoS ONE 2007; 2:e845.
5. Zeira E, Manevitch A, Manevitch Z, Kedar E, Gropp M, Daudi N, Barsuk R, et al. Femtosecond laser: a new intradermal DNA delivery method for efficient, long-term gene expression and genetic immunization. Faseb J 2007; 21:3522-3533.
6. Sanguino A, Lopez-Berestein G, Sood A K. Strategies for in vivo siRNA delivery in cancer. Mini Rev Med Chem 2008; 8:248-255.
7. Xu X, Yang L, Wang X, Chen X, Liang Q, Zeng J, Jing X. Ultrafine medicated fibers electrospun from W/O emulsions. J Control Release 2005; 108:33-42.
8. E L-v. Controlled release of heparin from poly(e-caprolactone) electrospun fibers. Biomaterials 2006; 27:2042-2050.
9. Verreck G, Chun I, Rosenblatt J, Peeters J, Dijck A V, Mensch J, Noppe M, et al. Incorporation of drugs in an amorphous state into electrospun nanofibers composed of a water-insoluble, nonbiodegradable polymer. J Control Release 2003; 92:349-360.
10. S G K. Recent Patents on Electrospun Biomedical Nanostructures: An Overview. Biomedical Engineering 2008; 1:68-78.
11. L I-C. COAXIAL ELECTROSPUN FIBERS AND STRUCTURES AND METHODS OF FORMING SAME. 2008.
12. Valenzuela M, Julian T B. Ductal carcinoma in situ: biology, diagnosis, and new therapies. Clin Breast Cancer 2007; 7:676-681.
13. Ali S. Multidimensional approaches in dealing with prostate cancer. Gene 2008; 410:1-8.
14. Damber J E, Aus G. Prostate cancer. Lancet 2008; 371: 1710-1721.
15. Marshall D T. Options and recent advances in permanent brachytherapy for prostate cancer. Can J Urol 2007; 14 Suppl 1:28-31.
16. Cheang M C, van de Rijn M, Nielsen T O. Gene expression profiling of breast cancer. Annu Rev Pathol 2008; 3:67-97.
17. Chang H. RNAi-mediated knockdown of target genes: a promising strategy for pancreatic cancer research. Cancer Gene Ther 2007; 14:677-685.
18. Cowgill S M, Muscarella P. The genetics of pancreatic cancer. Am J Surg 2003; 186:279-286.
19. Ming-Hsi Huang, Suming Li, Michel Vert, Synthesis and degradation of PLA-PCL-PLA triblock copolymer prepared by successive polymerization of 3-caprolactone and DL-lactide, Polymer 45 (2004) 8675-8681
20. Zheng-Ming Huang, et al, Encapsulating drugs in biodegradable ultrafine fibers through co-axial electrospinning Published online 3 Jan. 2006 in Wiley InterScience (www.interscience.wiley.com). DOI: 10.1002/jbm.a.30564
21. Sells M A, Chen M L, Acs G (1987) Production of hepatitis B virus particles in Hep G2 cells transfected with cloned hepatitis B virus DNA. Proc Natl Acad Sci USA 84: 1005-9.
22. Aoki Y, Aizaki H, Shimoike T, Tani H, Ishii K, et al. (1998) A human liver cell line exhibits efficient translation of HCV RNAs produced by a recombinant adenovirus expressing T7 RNA polymerase. Virology 250: 140-50.
23. Fellig Y, Almogy G, Galun E, Ketzinel-Gilad M (2004) A hepatocellular carcinoma cell line producing mature hepatitis B viral particles. Biochem Biophys Res Commun 321: 269-74.
24. Ariel I, Miao H Q, Ji X R, Schneider T, Roll D, et al. (1998) Imprinted H19 oncofetal RNA is a candidate tumour marker for hepatocellular carcinoma. Mol Pathol 51: 21-5.
25. Reynolds A, Leake D, Boese Q, Scaringe S, Marshall W S, et al. (2004) Rational siRNA design for RNA interference. Nat Biotechnol 22: 326-30.
26. Ayesh S, Matouk I, Schneider T, Ohana P, Laster M, et al. (2002) Possible physiological role of H19 RNA. Mol Carcinog 35: 63-74.
27. Ma'atuk et al, PLoS ONE. 2007 Sep. 5; 2(9):e845.

What is claimed is:

1. A method of treating a solid tumor in a subject, the method comprising the step of implanting an implant within said solid tumor or into a tumor bed thereof, wherein said implant is a solid matrix that has a volume between 0.1-1000 mm$^3$, and said solid matrix comprises:
   A. a biocompatible polymeric matrix, comprising a polymer selected from the group consisting of poly(glycolide-co-lactide) (PLGA), polylactic acid (PLA), polyglycolic acid (PGA), polyethylene glycol (PEG), and polycaprolactone (PCL); and
   B. an RNAi (RNA interference) agent that targets an oncogene or a tumor-promoting factor within said tumor, wherein said RNAi agent is incorporated within said biocompatible polymeric matrix and treats said tumor,
   wherein the amount of said RNAi agent is at least 1:20 weight/weight of the amount of said polymer in said biocompatible polymeric matrix.

2. The method according to claim 1, wherein said implant further comprises mannitol.

3. The method according to claim 1, wherein said RNAi agent is selected from the group consisting of a small interfering RNA (siRNA), a short hairpin RNA (shRNA), a Dicer-substrate siRNA (DsiRNA), a locked nucleic acid (LNA), a microRNA, and a non-coding RNA.

4. The method according to claim 1, wherein said oncogene is a mutated K-ras gene.

5. The method according to claim 4, wherein said mutated K-ras gene is K-ras G12D.

6. The method according to claim 1, wherein said RNAi agent is conjugated to a substance selected from the group consisting of cholesterol, palmitate, α-tocopherol (Vitamin E), a protein transduction domain, a membrane-penetrating peptide, a multi-component polymer system, and a lipophilic moiety.

7. The method according to claim 1, wherein said RNAi agent is complexed with a substance selected from the group consisting of a cationic peptide, spermin, phosphatidylethanolamine (cephalin), L-α-cephalin, DOTAP, DOPE, polyethyleneimine (PEI), a derivative of PEI, a polyamine, a cationic polymer, a lipid, a non-cationic polymer, and a natural polymer.

8. The method according to claim 1, wherein said implant is configured to be implantable using a needle and cylindrically shaped having a diameter between 17 gauge and 19 gauge.

9. The method according to claim 1, wherein the amount of said RNAi agent in said implant is at least 4 μg.

10. The method according to claim 1, wherein said implant further comprises polymeric fibers encapsulating said RNAi agent.

11. The method according to claim 1, wherein said biocompatible polymeric matrix comprises nanoparticles.

12. The method according to claim 1, wherein said implant further comprises a polymeric envelope.

13. A method of treating a solid tumor in a subject, the method comprising the step of implanting an implant within said solid tumor or into a tumor bed thereof, wherein said implant is a solid matrix that has a volume between 0.1-1000 mm$^3$, and said solid matrix comprises:
   A. a biocompatible polymeric matrix comprising poly(glycolide-co-lactide) (PLGA) and mannitol; and
   B. an RNAi (RNA interference) agent that targets an oncogene or a tumor-promoting factor within said tumor, wherein said RNAi agent is incorporated within said biocompatible polymeric matrix;
   wherein the amount of said RNAi agent is at least 1:20 weight/weight of the amount of said PLGA in said biocompatible polymeric matrix, and wherein said implant, when implanted into a subject's body tissue, treats said tumor and has an effective release period comprising 10 weeks.

14. The method according to claim 13, wherein said PLGA has a ratio of polylactic acid (PLA) and polyglycolic acid (PGA) of greater than 75:25.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
cttgtggtag ttggagctga                                             20
```

```
<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
ctgttctaga aggcaaatca c                                              21

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
accacagtcc atgccatcac                                                20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
tccaccaccc tgttgctgta                                                20
```